US012653501B2

(12) United States Patent (10) Patent No.: US 12,653,501 B2
Hu et al. (45) Date of Patent: Jun. 16, 2026

(54) ULTRASOUND IMAGE ACQUISITION AND PROCESSING PRESET SHARING, AND ASSOCIATED SYSTEMS, DEVICES, AND METHODS

(71) Applicant: KONINKLIJKE PHILIPS N.V., Eindhoven (NL)

(72) Inventors: Xiaowen Hu, Bothell, WA (US); Kyong Chang, Bothell, WA (US); Shannon Renee Fox, Everett, WA (US); Yanjun Gong, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 728 days.

(21) Appl. No.: 17/786,605

(22) PCT Filed: Dec. 8, 2020

(86) PCT No.: PCT/EP2020/085109
§ 371 (c)(1),
(2) Date: Jun. 17, 2022

(87) PCT Pub. No.: WO2021/122168
PCT Pub. Date: Jun. 24, 2021

(65) Prior Publication Data
US 2023/0020442 A1 Jan. 19, 2023

Related U.S. Application Data

(60) Provisional application No. 62/949,789, filed on Dec. 18, 2019.

(51) Int. Cl.
*A61B 8/00* (2006.01)

(52) U.S. Cl.
CPC ............ *A61B 8/4477* (2013.01); *A61B 8/467* (2013.01); *A61B 8/54* (2013.01)

(58) Field of Classification Search
CPC .................................. A61B 8/54; A61B 8/565
See application file for complete search history.

(56) References Cited

U.S. PATENT DOCUMENTS

| 6,377,162 B1 | 4/2002 | Delestienne et al. | |
| 2002/0057850 A1* | 5/2002 | Sirohey | H04N 19/33 375/E7.199 |

(Continued)

FOREIGN PATENT DOCUMENTS

| JP | 2004135926 A | 5/2004 |
| JP | 2005027813 A | 2/2005 |

(Continued)

OTHER PUBLICATIONS

International Search Report and Written Opinion for PCT/EP2020/085109, Mailing date: Feb. 22, 2021, 10 pages.

*Primary Examiner* — Jason M Ip

(57) ABSTRACT

Disclosed is an ultrasound imaging system that includes a remote server configured for communication with a first ultrasound imaging console and a second ultrasound imaging console. The server is configured to receive, from the first ultrasound imaging console, an upload request for a custom image setting, receive and store the custom image setting. The server is further configured to output, to the second ultrasound imaging console, data representative of the custom image setting; receive a request for the custom image setting; retrieve and send, to the second ultrasound imaging console, the custom image setting such that the second ultrasound imaging console can generate an image with the custom image setting.

19 Claims, 14 Drawing Sheets

(56)　　　　　References Cited

U.S. PATENT DOCUMENTS

| | | | |
|---|---|---|---|
| 2004/0138923 A1* | 7/2004 | Routh | G06Q 10/10 |
| | | | 709/200 |
| 2004/0204649 A1 | 10/2004 | Ramraj et al. | |
| 2006/0241455 A1 | 10/2006 | Shvarts | |
| 2008/0208045 A1 | 8/2008 | Rielly | |
| 2010/0274714 A1 | 10/2010 | Sims et al. | |
| 2013/0198143 A1 | 8/2013 | Matsumoto | |
| 2013/0198687 A1 | 8/2013 | Bird et al. | |
| 2019/0365359 A1 | 12/2019 | Teraoka et al. | |
| 2021/0059631 A1* | 3/2021 | Lewis | G06F 21/84 |

FOREIGN PATENT DOCUMENTS

| | | |
|---|---|---|
| JP | 2019179346 A | 10/2019 |
| JP | 2019209140 A | 12/2019 |

* cited by examiner

ULTRASOUND IMAGE ACQUISITION AND PROCESSING PRESET SHARING, AND ASSOCIATED SYSTEMS, DEVICES, AND METHODS

CROSS-REFERENCE TO PRIOR APPLICATIONS

This application is the U.S. National Phase application under 35 U.S.C. § 371 of International Application No. PCT/EP2020/085109, filed on Dec. 8, 2020, which claims the benefit of U.S. Provisional Patent Application No. 62/949,789, filed on Dec. 18, 2019. These applications are hereby incorporated by reference herein.

TECHNICAL FIELD

The subject matter described herein relates to distributed network based sharing of ultrasound image capture and postprocessing settings between remote ultrasound imaging consoles. This ultrasound setting sharing system has particular but not exclusive utility for medical diagnostic imaging in human patients.

BACKGROUND

External ultrasound imaging devices have become indispensable diagnostic tools in modern day medical care due to their non-invasive nature and ever-increasing resolution. Because different tissues within the body have different density and water content, they reflect sound waves differently, and thus appear different from one another on an ultrasound image. Ultrasound images can be captured or postprocessed with various image settings that affect the contrast, definition, and resolution of different tissues or other features within the image. Thus, ultrasound imaging involves several factory presets to optimize imaging parameters for particular imaging tasks.

In many cases, users desire to adjust image settings to suit their specific clinical needs, such that they differ from factory default image settings, or factory preset files containing groups of settings for a particular application (e.g., presets for imaging particular organs of the body). Users may request changes to the default settings or factory preset files from the manufacturer. However, software updates for ultrasound imaging systems may occur less frequently, and in many cases must be installed by a qualified technician. This results in a longer latency between user complaints and the arrival of potential solutions, which may decrease users' satisfaction with the ultrasound system.

A current method to address users' different image quality requirements is for the manufacturer to send a technician to a user's site and create one or more custom settings to address the user's image quality concerns. This may require multiple visits to solve problems iteratively, which is not cost effective. In some cases, skilled users can also create their own custom settings manually. Once a setting is selected for a particular imaging mode, a user can then refine the parameters from the preset baseline to achieve the desired imaging settings. However, many users struggle to refine the parameters to achieve the best imaging quality, and this can cause several issues: 1) poor image quality; 2) lack of consistency between users; 3) a prolonged process of training workers for image optimization; 4) a prolonged process in identifying preset issues that impact a large customer base. Currently, systems do not exist for users to share setting files back to the manufacturer, for the manufacturer to learn how their equipment is being used. Systems also do not exist for different users to be able to share custom setting files with one another.

In addition, users from different regions or specialties, with different education backgrounds and previous experience, may have different image quality preferences or requirements. Currently, the manufacturers of ultrasound imaging equipment do not offer region-specific factory settings. In order to provide region-specific or specialty-specific factory settings, a manufacturer needs to understand the image quality preferences for a specific region or a group of users. Currently, this is done through customer visits and customer reports, but due to small sample size, the manufacturers may not develop a good understanding of the customers' requirements.

The information included in this Background section of the specification, including any references cited herein and any description or discussion thereof, is included for technical reference purposes only and is not to be regarded as subject matter by which the scope of the disclosure is to be bound.

SUMMARY

Disclosed is a system for sharing image capture and postprocessing settings for an external ultrasound console. A remote server communicates with multiple ultrasound imaging consoles, each with an imaging probe that obtains ultrasound imaging data. The ultrasound imaging console allows a user to adjust individual parameters or controls related to acquisition of the ultrasound imaging data by the probe and/or processing of the imaging data to generate an ultrasound image. A user designates, on the console he or she is using, a custom image setting that includes particular values of the acquisition and/or processing parameters that allow the user to obtain an ultrasound image of the desired image quality. Utilizing a form of distributed network system (e.g., server-client or cloud), this custom image setting is uploaded from the console to the server. The server stores this custom image setting and makes it available to other remote users. A remote user at a different ultrasound imaging console downloads the custom image setting, which is applied by the different console to control acquisition and/or processing of ultrasound imaging data collected by the remote user's probe. Thus, users at different locations can upload and download custom image settings using the server. Providing the server to share ultrasound custom image settings advantageously provides rapid dissemination of desirable settings for good image quality, such as region-specific and/or specialty-specific settings.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect of the ultrasound setting sharing system includes an ultrasound imaging system, including: a server comprising a processor in communication with a memory, wherein the server is configured for communication with and remote from a first ultrasound imaging console and a second ultrasound imaging console, wherein the server is configured to: receive, from the first ultrasound imaging console, an upload request for a custom image setting; receive, from the first ultrasound imaging console, the custom image setting; store the custom image setting in the memory; output, to the second ultrasound imaging console, data representative of the custom image setting; receive, from the second ultrasound imaging console, a request for the custom image setting; retrieve, from the memory, the custom image setting in response to the request; and output, to the second ultrasound imaging console, the custom image setting such that the second ultrasound imaging console is configured to generate a first ultrasound image with the custom image setting. Other embodiments of this aspect include corresponding computer systems, apparatus, and computer programs recorded on one or more computer storage devices, each configured to perform the actions of the methods.

Implementations may include one or more of the following features. The ultrasound imaging system further comprising: the first ultrasound imaging console; the second ultrasound imaging console; a first ultrasound imaging probe in communication with the first ultrasound imaging console; and a second ultrasound imaging probe in communication with the second ultrasound imaging console. The ultrasound imaging system where the custom image setting is different than a manufacturer image setting. The ultrasound imaging system where the server is configured to: receive, from a plurality of ultrasound imaging consoles, a plurality of requests to upload a plurality of custom image settings; receive, from the plurality of ultrasound imaging consoles, the plurality of custom image settings; store the plurality of custom image settings in the memory; output, to the plurality of ultrasound imaging consoles, data representative of each of the plurality of custom image settings; receive, from one or more of the plurality of ultrasound imaging consoles, a selection of one or more of the plurality of custom image settings to download; and output, to the one or more of the plurality of ultrasound imaging consoles, the one or more of the plurality of custom image settings. The ultrasound imaging system where the server is configured to: receive, from a manufacturer system, a manufacturer image setting; store the manufacturer image setting in the memory; output, to a plurality of ultrasound imaging consoles, data representative of the manufacturer image setting; receive, from one or more of the plurality of ultrasound imaging consoles, a selection of the manufacturer image setting to download; and output, to the one or more of the plurality of ultrasound imaging consoles, the manufacturer image setting. The ultrasound imaging system further comprising the first ultrasound imaging console, wherein the first ultrasound imaging console comprises a further processor and a display, wherein the further processor is configured to output, to the display, a graphical user interface (GUI) comprising an indication of the custom image setting and an upload option, wherein the further processor is configured to output the upload request to the server based on user selections of the indication of the custom image setting and the upload option. The ultrasound imaging system where the further processor is configured to receive a user input, via the GUI, to modify the custom image setting. The ultrasound imaging system where the first ultrasound imaging console comprises a further memory, wherein the further processor is configured to: store the custom image setting in the further memory; retrieve the custom image setting from the memory based on the upload request; and output the custom image setting to the server. The ultrasound imaging system further comprising the second ultrasound imaging console, wherein the second ultrasound imaging console comprises a further processor and a display, wherein the further processor is configured to output, to the display, a graphical user interface (GUI) comprising a download option and an indication of the custom image setting based on the data representative of the custom image setting, wherein the further processor is configured to output the request to the server based on user selections of the download option and the indication of the custom image setting. The ultrasound imaging system of claim 9, wherein the second ultrasound imaging console comprises a further memory, wherein the further processor of the second ultrasound imaging console is configured to: store the custom image setting in the further memory; retrieve the custom image setting from the further memory based on an implementation request; and apply the custom image setting to generate a second image with the custom image setting. The ultrasound imaging system where the server is configured to output, to the second ultrasound imaging console, an ultrasound imaging preview corresponding to application of at least one of the custom image setting or a further custom image setting. The ultrasound imaging system further comprising: the first ultrasound imaging console; and the second ultrasound imaging console, wherein the first ultrasound imaging console is configured to be positioned within a first patient examination area and the second ultrasound imaging console is configured to be positioned within a second patient examination area spaced from the first patient examination area. The ultrasound imaging system where the custom image setting comprises at least one of an acquisition parameter associated with operation of an ultrasound imaging probe to acquire ultrasound imaging data or a post-processing parameter associated with processing of the ultrasound imaging data to generate the first ultrasound image. Implementations of the described techniques may include hardware, a method or process, or computer software on a computer-accessible medium.

One general aspect includes an ultrasound imaging method, including: receiving, at a server comprising a processor in communication with a memory, an upload request for a custom image setting, wherein the server is in communication with and remote from a first ultrasound imaging console and a second ultrasound imaging console, wherein the upload request is received from the first ultrasound imaging console; receiving, at the server, the custom image setting from the first ultrasound imaging console; storing the custom image setting in the memory; outputting, by the server, data representative of the custom image setting to the second ultrasound imaging console; receiving, at the server, a request for the custom image setting from the second ultrasound imaging console; retrieving, from the memory, the custom image setting in response to the request; and outputting, by the server, the custom image setting to the second ultrasound imaging console such that the second ultrasound imaging console generates an image with the custom image setting. Other embodiments of this aspect include corresponding computer systems, apparatus, and computer programs recorded on one or more computer storage devices, each configured to perform the actions of the methods.

Implementations may include one or more of the following features. The ultrasound imaging method wherein the custom image setting comprises at least one of an acquisition parameter associated with operation of an ultrasound imaging probe to acquire ultrasound imaging data or a post-processing parameter associated with processing of the ultrasound imaging data to generate the ultrasound image. The ultrasound imaging method further comprising receiving, at the server, a plurality of requests to upload a plurality of custom image settings from a plurality of ultrasound imaging consoles; receiving, at the server, the plurality of custom image settings from the plurality of ultrasound imaging consoles; storing the plurality of custom image settings in the memory; outputting, by the server, data representative of each of the plurality of custom image settings to the plurality of ultrasound imaging consoles; receiving, at the server, a selection of one or more of the plurality of custom image settings to download from one or more of the plurality of ultrasound imaging consoles; and outputting, by the server, the one or more of the plurality of custom image settings to the one or more of the plurality of ultrasound imaging consoles. The ultrasound imaging method further comprising: receiving, at the server, a manufacturer image setting from a manufacturer system; storing the manufacturer image setting in the memory; outputting, from the server, to a plurality of ultrasound imaging consoles, data representative of the manufacturer image setting; receiving, at the server, a selection of the manufacturer image setting to download from one or more of the plurality of ultrasound imaging consoles; and outputting, by the server, the manufacturer image setting to the one or more of the plurality of ultrasound imaging consoles. The ultrasound imaging method further comprising: outputting, by a further processor of the first ultrasound imaging console, a graphical user interface (GUI) to a display of the first ultrasound imaging console, wherein the GUI comprises an indication of the custom image setting and an upload option; and outputting, by the further processor, the upload request to the server based on user selections of the indication of the custom image setting and the upload option. The ultrasound imaging method further comprising receiving, at the further processor, a user input to modify the custom image setting via the GUI. The ultrasound imaging method further comprising storing the custom image setting in a further memory of the first ultrasound imaging console; retrieving, by the further processor, the custom image setting from the memory based on the upload request; and outputting, by the further processor, the custom image setting to the server. The ultrasound imaging method further including: outputting, by a further processor of the second ultrasound imaging console, a graphical user interface (GUI) to a display of the second ultrasound imaging console, where the GUI includes a download option and an indication of the custom image setting based on the data representative of the custom image setting; and outputting, by the further processor, the request to the server based on user selections of the download option and the indication of the custom image setting. The ultrasound imaging method further including: storing the custom image setting in the further memory of the second ultrasound imaging console; retrieving, by the further processor, the custom image setting from the further memory based on an implementation request; and applying, by the further processor, the custom image setting to at least one of operate the ultrasound imaging probe to acquire the ultrasound imaging data based on the acquisition parameter or generate the second ultrasound image by processing the ultrasound data based on the post-processing parameter. The ultrasound imaging method where the server is configured to output an ultrasound imaging preview to the second ultrasound imaging console, where the ultrasound imaging preview corresponds to application of at least one of the custom image setting or a further custom image setting. Implementations of the described techniques may include hardware, a method or process, or computer software on a computer-accessible medium.

The ultrasound setting/preset sharing system disclosed herein has particular, but not exclusive, utility for medical diagnostic imaging of human patients.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the ultrasound setting/preset sharing system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
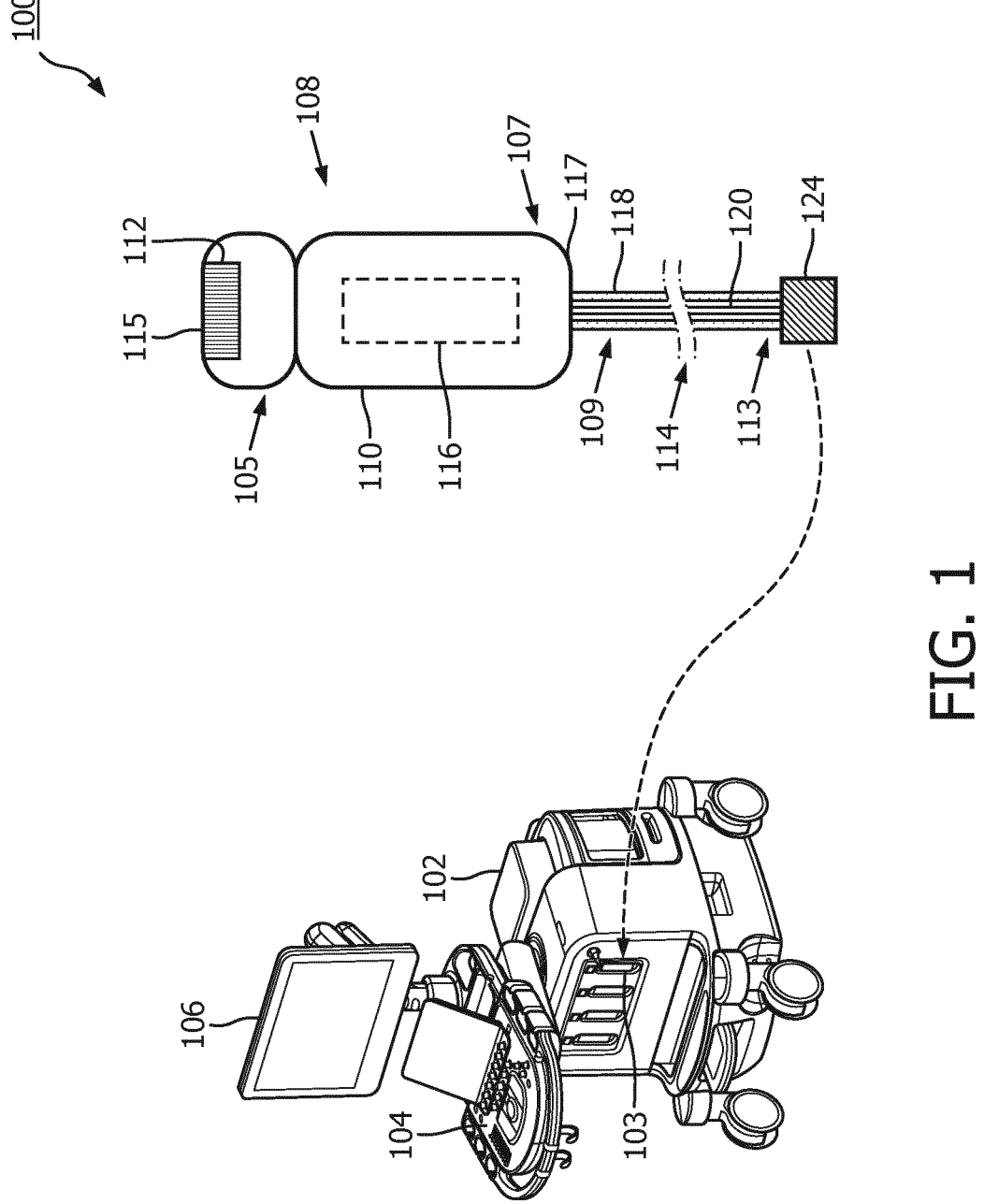
FIG. 1 is a diagrammatic perspective view of an ultrasound imaging system, according to aspects of the present disclosure.

Disclosed is a system for sharing image capture and postprocessing setting for an external ultrasound console, hereinafter known as an ultrasound setting/preset sharing system, that advantageously provides a system and process for users of ultrasound imaging systems to acquire new imaging expertise from multiple sources. The ultrasound setting/preset sharing system includes an ultrasound probe, comprising: a housing configured for handheld operation by a user; a transducer array coupled to the housing and configured to obtain ultrasound data; a cable coupled to the housing, wherein the cable comprises a conduit and a plurality of electrical conductors in communication with the transducer array, wherein the plurality of electrical conductors comprises a distal portion disposed within the housing and a proximal portion disposed within the conduit; and a computer in communication with the transducer array via the plurality of electrical conductors and configured to generate an ultrasound image based on the ultrasound data, and to display it on a display. The ultrasound preset sharing system also includes systems, devices, and methods for modifying factory image presets, storing them as custom image setting files, and sharing them across a network through a remote server. Since custom setting files are based on manufacturer preset or manufacturer image setting files, it may be possible for a manufacturer to distribute custom setting files, or for customers to share custom setting files with one another, without a need for separate regulatory clearance for each file or group of files. A custom image setting can be one or a plurality of selected image capture and/or postprocessing parameters. A custom image setting can also be referred to as a preset or a preset setting in some instances. For example, a preset or a preset setting can a pre-programmed image setting, such as a factory setting. In some instances, a custom image setting can a user's selection of parameters that is different than the factory selection of parameters.

The ultrasound preset sharing system streamlines customized ultrasound image settings for customers by pooling image setting data from a population of users, in which the image parameter data includes a deviation from a system preset. Using the pooled image setting data, the ultrasound preset sharing system provides a database allowing other users access to one another's image setting data and/or generating customized presets based on the pooled image parameter data. The system can retrieve user image settings from a first user, along with image data corresponding to the user image settings, wherein the user image settings are different from the manufacturer's default image settings or manufacturer-defined image setting presets. Manufacturer's presets may be distributed with a new system, or may be distributed through a network by an imaging console, a server, or other manufacturer-controlled computing system. The system can also store the user image settings to a database existing on a computer memory accessible by multiple users, and can generate a report for the user image settings, the report comprising at least a comparison of the user image setting and the preset image setting and being accessible on the database, and can further customize the user image setting based on the report, thereby creating a customized user setting, and allow a second user to select the user image setting or customized user image setting for subsequent imaging.

In this way, the ultrasound preset sharing system permits users to learn from each other. Users may have an easier time accepting a preset that is shared by a physician or an institution they know of. One scenario is that user A is an ultrasound doctor in Hospital A. He or she isn't satisfied with the performance of a "small part" factory preset, and so he or she searches the database on a manufacturer-controlled server to see if there is any "small part" custom preset shared by other users. He or she finds there is a custom preset for small parts shared by the ultrasound director in Hospital B.

Hospital B is one of the most famous hospitals in China, specializing in small part imaging. User A downloads this preset and starts to use it to see if it provides the desired image quality for imaging small parts. In some cases, the download may be of the complete custom imaging setting (e.g., as a custom image setting file file). In such instances, the custom image setting may be stored in a persistent and/or non-volatile memory on the console and available for use in any future imaging procedure by the console. In other cases, the download may be downloading a temporary cache or temporary cache file including all or at least part of the custom image setting. In such instances, the custom image setting may be stored in a volatile memory and available for use in the current procedure. Such temporary cache files may advantageously provide a user with the ability to try multiple custom image settings that are available for download, without having to download and store all of them locally on the ultrasound imaging console. For example, the console can download and locally apply the temporary cache file to ultrasound imaging data to generate a preview of how the custom image setting would generate the ultrasound image.

The present disclosure aids clinicians and other users substantially in obtaining a desired ultrasound image quality, by improving user access to image settings customized for a particular application or region. Implemented on a processor in communication with a remote server via a wide-area network, the ultrasound preset sharing system disclosed herein provides users with practical access to the image settings customization effort and experience of other users of the system. This improved information exchange transforms a laborious process of individual customization into a straightforward process of comparison and selection, without the normally routine need to wait for manufacturer-issued software updates. This unconventional approach improves the functioning of the ultrasound imaging system, by ensuring that the best possible image presets are available to each registered user.

The ultrasound preset sharing system may be implemented as a menu system accessing a remote server and viewable on a display, and operated by a control process executing on a processor that accepts user inputs (e.g., from a keyboard, mouse, or touchscreen interface), and that is in communication with a processor of one or more additional users. In that regard, the control process performs certain specific operations in response to different inputs or selections made at different points in the process of using the system. Certain structures, functions, and operations of the processor, display, sensors, and user input systems are known in the art, while others are recited herein to enable novel features or aspects of the present disclosure with particularity.

These descriptions are provided for exemplary purposes only, and should not be considered to limit the scope of the ultrasound preset sharing system. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic perspective view of an ultrasound imaging system 100, according to aspects of the present disclosure. The ultrasound imaging system 100 includes a console 102 and an ultrasound probe 108. The ultrasound imaging system 100 may be used to obtain and display ultrasound images of anatomy. In some circumstances, the system 100 may include additional elements and/or may be implemented without one or more of the elements illustrated in FIG. 1.

The ultrasound probe 108 is sized and shaped, structurally arranged, and/or otherwise configured to be placed on or near the anatomy of a subject to visualize anatomy inside of the subject's body. The subject may be a human patient or animal. The ultrasound probe 108 may be positioned outside the body of the subject. In some embodiments, the ultrasound probe 108 is positioned proximate to and/or in contact with the body of the subject. For example, the ultrasound probe 108 may be placed directly on the body of the subject and/or adjacent to the body of the subject. The view of the anatomy shown in the ultrasound image depends on the position and orientation of the ultrasound probe 108. To obtain ultrasound data of the anatomy, the ultrasound probe 108 can be suitably positioned and oriented by a user, such as a physician, sonographer, and/or other medical personnel, so that a transducer array 112 emits ultrasound waves and receives ultrasound echoes from the desired portion of the anatomy. The ultrasound probe 108 may be portable and suitable for use in a medical setting. In some instances, the ultrasound probe 108 can be referenced as an ultrasound imaging device, a diagnostic imaging device, external imaging device, transthoracic echocardiography (TTE) probe, and/or combinations thereof.

The ultrasound probe 108 includes a housing 110 structurally arranged, sized and shaped, and/or otherwise configured for handheld grasping by a user. The housing 110 can be referenced as a handle in some instances. A proximal portion 107 of the housing 110 can be referenced as a handle in some instances. The housing 110 surrounds and protects the various components of the imaging device 108, such as electronic circuitry 116 and the transducer array 112. Internal structures, such as a space frame for securing the various components, may be positioned within the housing 110. In some embodiments, the housing 110 includes two or more portions which are joined together during manufacturing. The housing 110 can be formed from any suitable material, including a plastic, a polymer, a composite or combinations thereof.

The housing 110 and/or the ultrasound probe 108 includes the proximal portion 107 terminating at a proximal end 117 and a distal portion 105 terminating at a distal end 115. In some instances, the ultrasound probe 108 can be described as having the proximal portion 107 and the distal portion 105. An imaging assembly of the ultrasound probe 108, including the transducer array 112, is disposed at the distal portion 105. All or a portion of the imaging assembly of the ultrasound probe 108 can define the distal end 115. The transducer array 112 can be directly or indirectly coupled to the housing 110. The operator of the ultrasound probe 108 may contact the distal end 115 of the ultrasound probe 108 to the body of the patient such that the anatomy is compressed in a resilient manner. For example, the imaging assembly, including the transducer array 112, may be placed directly on or adjacent to the body of the subject. In some instances, the distal portion 105 is placed directly in contact with the body of the subject such that the transducer array 112 is adjacent to the body of the subject.

The ultrasound probe 108 is configured to obtain ultrasound imaging data associated with any suitable anatomy of the patient. For example, the ultrasound probe 108 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, and/or other systems of the body. The anatomy may be a blood vessel, such as an artery or a vein of a patient's vascular system, including cardiac vasculature, peripheral vasculature, neural vasculature, renal vasculature, and/or any other suitable lumen inside the body. In addition to natural structures, the ultrasound probe 108 may be used to examine man-made structures such as, but without limitation, heart valves, stents, shunts, filters and other devices.

The transducer array 112 is configured to emit ultrasound signals, and receive ultrasound echo signals corresponding to the emitted ultrasound signals. The echo signals are reflections of the ultrasound signals from anatomy with the subject's body. The ultrasound echo signals may be processed by the electronic circuitry 116 in the ultrasound probe 108 and/or in the console 102 to generate ultrasound images. The transducer array 112 is part of the imaging assembly of the ultrasound probe 108, including an acoustic window/lens and a matching material on a transmitting side of the transducer array 112, and an acoustic backing material on a backside of the transducer array 112. The acoustic window and the matching material have acoustic properties that facilitate propagation of ultrasound energy in desired directions (e.g., outwards, into the body of the patient) from the transmitting side of the transducer array 112. The backing material has acoustic properties that impede or limit propagation of ultrasound energy in undesired directions (e.g., inwards, away from the body of the patient) from the backside of the transducer array 112.

The transducer array 112 may include any number of transducer elements. For example, the array can include between 1 acoustic element and 10000 acoustic elements, including values such as 2 acoustic elements, 4 acoustic elements, 15 acoustic elements, 64 acoustic elements, 128 acoustic elements, 500 acoustic elements, 812 acoustic elements, 3000 acoustic elements, 9000 acoustic elements, and/or other values both larger and smaller. The transducer elements of the transducer array 112 may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., arranged in one or more rows, one or more columns, and/or one or more orientations) can be uniformly or independently controlled and activated. The transducer array 112 can be configured to obtain one-dimensional, two-dimensional, and/or three-dimensional images of patient anatomy. The ultrasound transducer elements may be piezoelectric/piezoresistive elements, piezoelectric micromachined ultrasound transducer (PMUT) elements, capacitive micromachined ultrasound transducer (CMUT) elements, and/or any other suitable type of ultrasound transducer elements.

The transducer array 112 is in communication with (e.g., electrically coupled to) the electronic circuitry 116. The electronic circuitry 116 can be any suitable passive or active electronic components, including integrated circuits (ICs), for controlling the transducer array 112 to obtain ultrasound imaging data and/or processing the obtained ultrasound imaging data. For example, the electronic circuitry 116 can include one or more transducer control logic dies. The electronic circuitry 116 can include one or more application specific integrated circuits (ASICs). In some embodiments, one or more of the ICs can comprise a microbeamformer (µBF), an acquisition controller, a transceiver, a power circuit, a multiplexer circuit (MUX), etc. In some embodiments, the electronic circuitry 116 can include a processor, a memory, a gyroscope, and/or an accelerometer. The electronic circuitry 116 is disposed within the ultrasound probe 108 and surrounded by the housing 110.

The ultrasound probe 108 includes a cable 114 to provide signal communication between the console 102 and one or more components of the ultrasound probe 108 (e.g., the transducer array 112 and/or the electronic circuitry 116). The cable 114 includes multiple electrical conductors 120 configured to carry electrical signals between the console 102 and the ultrasound probe 108. The electrical conductors 120 can be bare wires surrounded by one or more layers of insulating materials. The insulating materials are typically polymer-based composites, nylon, and/or polyvinyl chloride (PVC) synthetic plastic polymer. For example, electrical signals representative of the imaging data obtained by the transducer array 112 can be transmitted from the ultrasound probe 108 to the console 102 via the electrical conductors 120. Control signals and/or power can be transmitted from the console 102 to the ultrasound probe 108 via the electrical conductors 120. The cable 114 and/or electrical conductors 120 may provide any type of wired connection, such as a proprietary connection, an Ethernet connection, a Universal Serial Bus (USB) connection of any version or a mini USB of any version.

The cable 114 can also include a conduit 118 surrounding the electrical conductors 120. The conduit 118 is shaped as a tube and used to protect and route the electrical conductors 120 in the cable 114 of the ultrasound imaging device 108. The conduit 118 can be flexible and made of polymer, plastic, metal, fiber, other suitable materials, and/or combinations thereof. The conduit 118 protects the electrical conductors 120 by preventing their direct exposure to outside elements. A distal portion 109 of the cable 114 is coupled to the proximal portion 107 of the housing 110 of the ultrasound probe 108.

A connector 124 is located at a proximal portion 113 of the cable 114. The connector 124 is configured for removably coupling with the console 102. Signal communication between the ultrasound probe 108 and the console 102 is established when the connector 124 is received within a receptacle 103 of the console 102. In that regard, the ultrasound probe 108 can be electrically and/or mechanically coupled to the console 102. The console 102 can be referenced as a computer or a computing device in some instances. The console 102 includes a user interface 104 and a display 106. The console 102 is configured to process the ultrasound imaging data obtained by the ultrasound probe 108 to generate an ultrasound image and output the ultrasound image on the display 106. A user can control various aspects of acquiring ultrasound imaging data by the ultrasound probe 108 and/or display of ultrasound images by providing inputs at the user interface 104. The imaging device 108 and the display 106 may be communicatively coupled directly or indirectly to the console 102.

One or more image processing steps can be completed by the console 102 and/or the ultrasound probe 108. The console 102 and/or the ultrasound probe 108 can include one or more processors in communication with memory. The processor may be an application-specific integrated circuit (ASIC), a field-programmable gate array (FPGA), a central processing unit (CPU), a digital signal processor (DSP), another hardware device, a firmware device, or any combination thereof configured to perform the operations described herein. In some embodiments, the memory is a random access memory (RAM). In other embodiments, the memory is a cache memory (e.g., a cache memory of the processor), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory may include a non-transitory computer-readable medium. The memory may store instructions. The instructions may include instructions that, when executed by a processor, cause the processor to perform operations described herein.

While the console 102 is a movable cart in the illustrated embodiment of FIG. 1, it is understood that the console 102 can be a mobile device (e.g., a smart phone, a tablet, a laptop, or a personal digital assistant (PDA)) with integrated processor(s), memory, and display. For example, a touch-screen of the mobile device can be the user interface 104 and the display 106.

Before continuing, it should be noted that the examples described above are provided for purposes of illustration, and are not intended to be limiting. Other devices and/or device configurations may be utilized to carry out the operations described herein.

Figure 2:
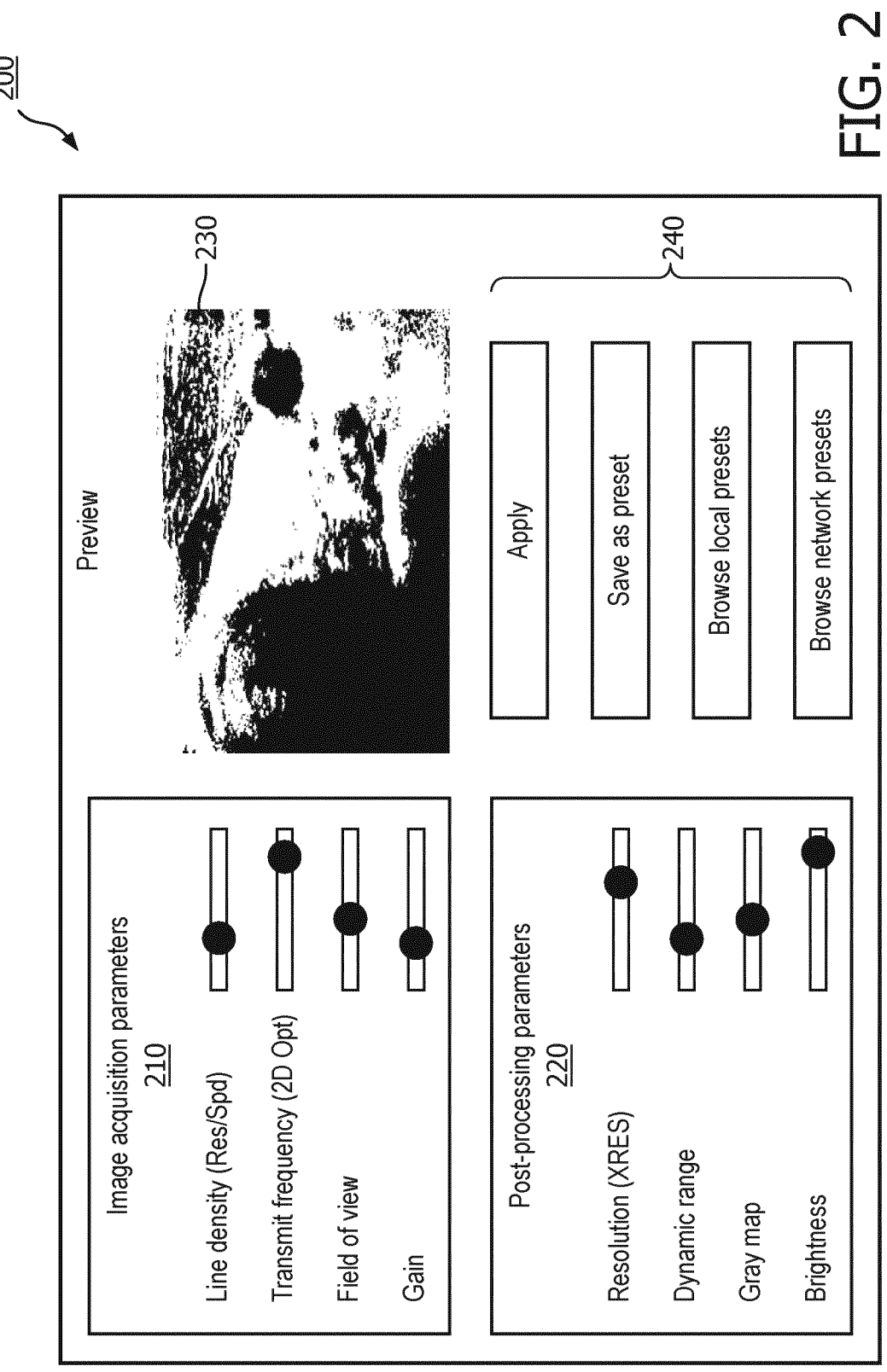
FIG. 2 is a display screen of an example ultrasound preset sharing system, according to at least one embodiment of the present disclosure.

FIG. 2 is a display screen 200 of an example ultrasound preset sharing system, according to at least one embodiment of the present disclosure. The display screen 200 allows users to adjust image acquisition parameters 210 and image post-processing parameters 220. Image acquisition parameters 210 affect the operation of the ultrasound transducer array 112, and may include but are not limited to line density, transmission frequency, field of view, depth of view, and gain. Line density can refer to the angular distance between scan lines in an ultrasound image, or the number of ultrasound beams or pulses that are used to interrogate the field of view in the ultrasound image. Increasing the line density can increase the spatial resolution of the image, but may decrease the temporal resolution and/or frame rate. Decreasing the line density can decrease the spatial resolution of the image, but may increase the temporal resolution and/or frame rate. Transmission frequency can refer to the frequency (e.g., the inverse of the wavelength) of the acoustic waves or pulses generated by the ultrasound scanner. Higher frequencies may be associated with greater spatial resolution, but also greater absorption/attenuation of the signal by tissues, whereas lower frequencies may be associated with lower resolution but greater reflection, and thus greater amplitude of the returned echoes. Field of view can refer to the angular window (e.g., in degrees or radians) of the ultrasound scanner. A larger field of view may see more in a given image, but take longer to capture, whereas a smaller field of view shows less in each frame, but may permit frames to be captured at a higher rate. Depth of view refers to the depth the ultrasound signal is expected or desired to penetrate into tissues. If the desired depth of view is increased, each image can show more of the tissue being scanned, but the time between pulses (e.g., scan lines) must be increased, due to pulses propagating at the speed of sound over a longer outbound path and return path. Thus, scan depth is inversely proportional to frame rate. Gain is an amplification of the return signal from each ultrasound pulse or scan line, and can be used for example to compensate for attenuation. Increased gain results in a stronger signal (e.g., a brighter image) but also more noise (e.g., speckling) and reduced image contrast.

Image post-processing parameters 220 do not affect the operation of the ultrasound transducer array, but do affect the way captured images are shown on the display 106. Image post-processing parameters 220 may include, but are not limited to, resolution, dynamic range, gray map, color map, brightness, contrast, smoothness/sharpness, and ringdown removal. Resolution can refer to the number of pixels used to display a particular image. Higher resolution may be associated with a more detailed image and lower frame rate, whereas lower resolution may be associated with a less detailed image and a higher frame rate. Dynamic range can refer to the total range of intensities of a return signal. A large dynamic range may be capable of displaying fainter details in an ultrasound image (which may be indicative of lower tissue density), but with greater noise, whereas a small dynamic range may preferentially show only tissues of a particular density or composition. Contrast can refer to the difference in displayed brightness between pixels of different signal strength. High contrast can be associated with greater definition between areas of different density, and reduced definition between areas of similar density. Smoothness and sharpness are opposite parameters that define how clearly edges are defined between areas of different signal strength. High sharpness can result in a clearer image but greater noise, and can reduce the appearance of certain features while enhancing the appearance of others. Ringdown can refer to secondary or harmonic echoes that carry information about tissue density and composition, but may distort the ultrasound image. Ringdown removal uses image processing to remove ringdown artifacts from the image.

In this example, a preview pane 230 is provided, and displays a series of ultrasound images that are captured in real time such that the effects of different image acquisition parameters 210 and image post-processing parameters 220 can be seen in real time. The display screen 200 also includes file controls 240, that permit the current image acquisition parameters 210 and image post-processing parameters 220 to be applied to the current image or imaging procedure, saved as a preset file, or to be replaced with a preset file that has been stored either locally or on a remote server. If a user opts to save the current parameters 210 and 220 as a preset file, the user will be prompted for an author name (e.g., "Dr. John Smith"), a filename (e.g., "John Smith Cambridge Bone Screw Ultrasound Parameters") and description, that will be saved along with the currently selected parameters 210 and 220. In some embodiments, the system may also require the user to upload example images, either in a PC format (e.g., a JPEG), or in a medical industry format (e.g., Dicom).

An image preset can include image acquisition parameters, post-processing parameters, or combinations thereof. Depending on the implementation, modifying the parameters within a preset may include modifying one or more values of the parameters, adding parameters, or removing parameters that are included in the preset.

Figure 3A:
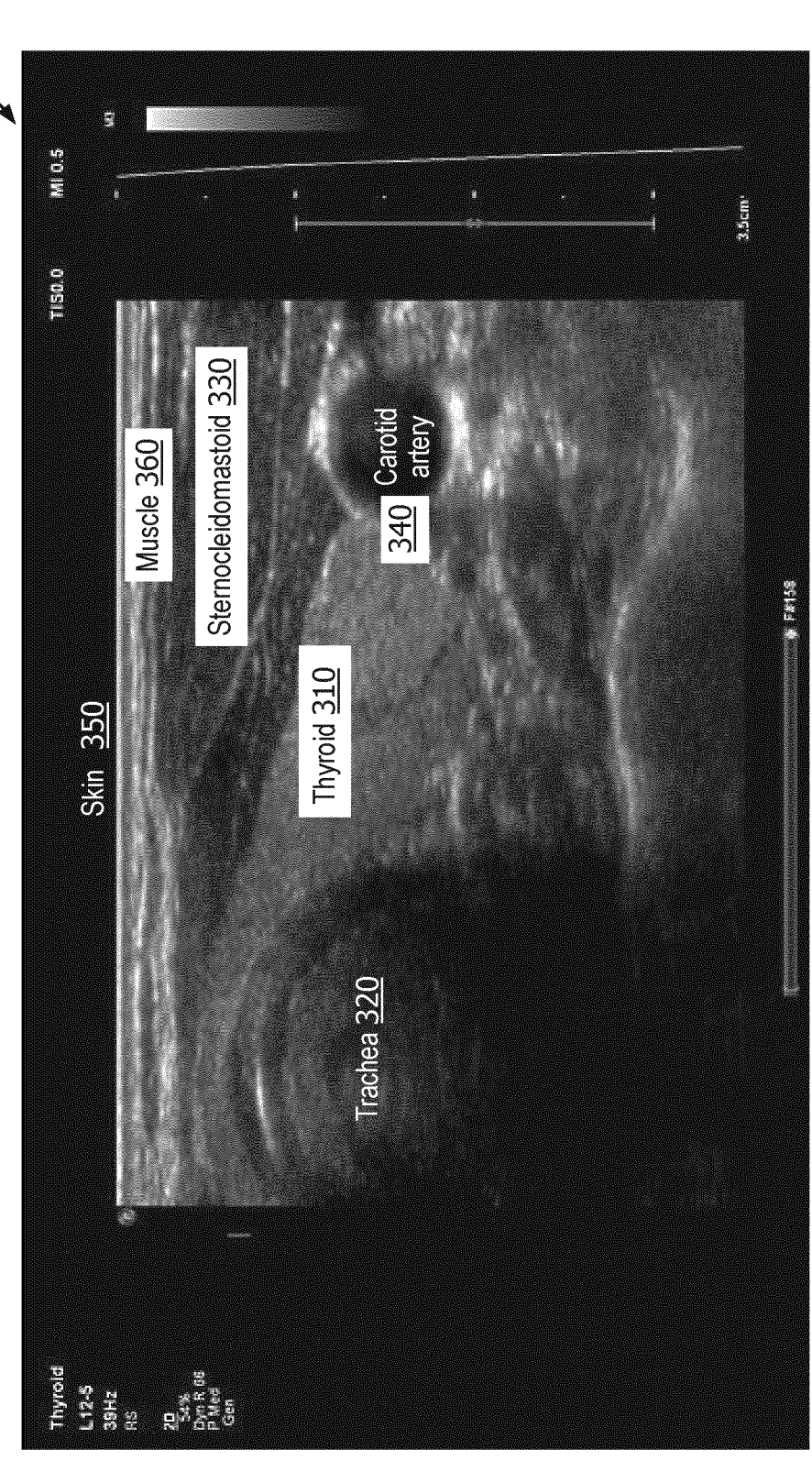
FIG. 3a is a screenshot of an external ultrasound image of a human thyroid, captured using default imaging parameters.

FIG. 3a is a screenshot of an external ultrasound image 300 of a human thyroid, captured using default imaging parameters. Visible are the left lobe and isthmus of the thyroid 310, along with the trachea 320, sternocleidomastoid 330, and carotid artery 340. The isthmus of the thyroid 310 extends over the trachea 320, toward the right lobe of the thyroid (not pictured). The image shows room for improvement in spatial resolution and uniformity.

Figure 3B:
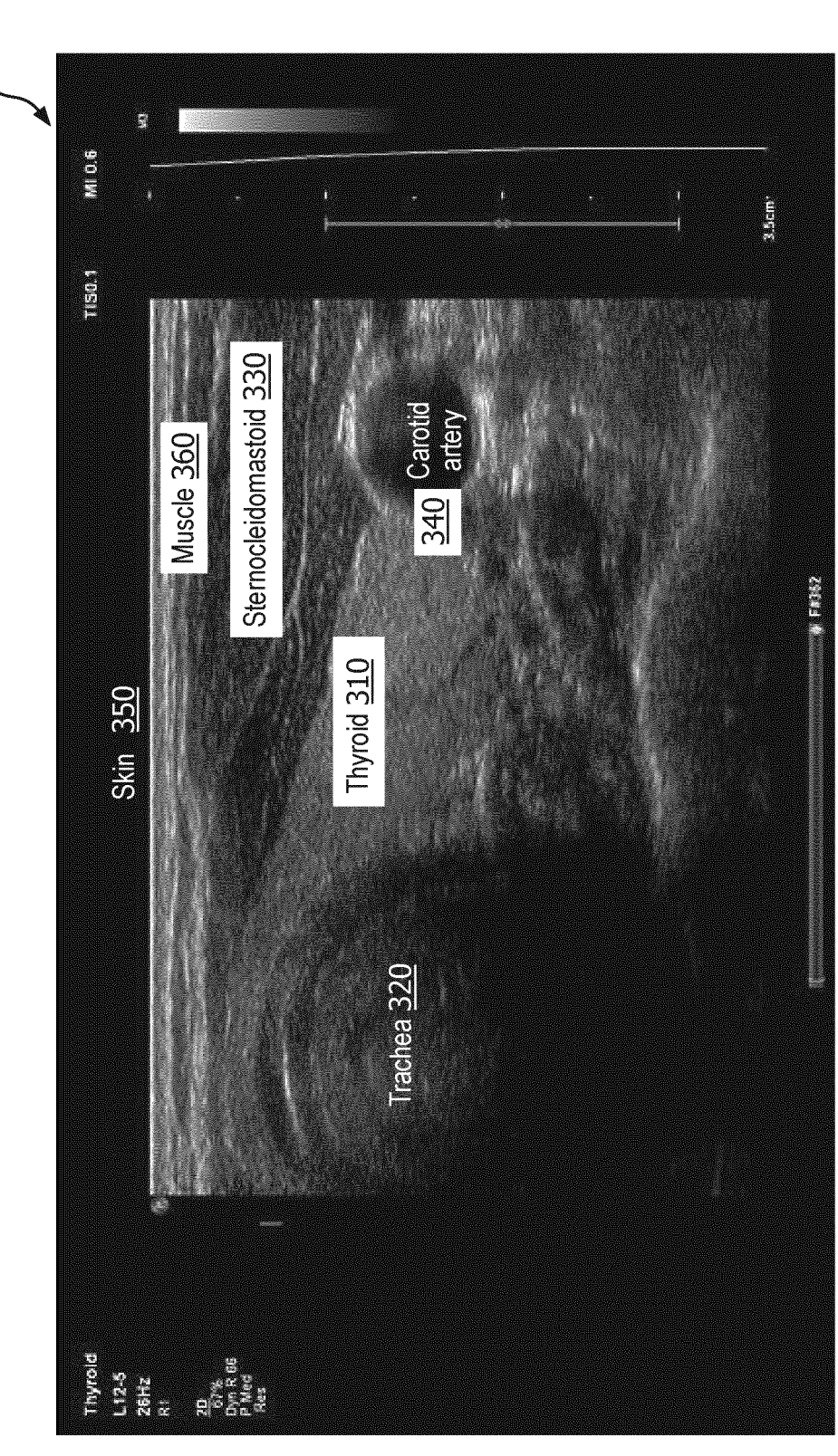
FIG. 3b is a screenshot of an external ultrasound image of the same human thyroid shown in FIG. 3a, but with different image acquisition parameters.

FIG. 3b is a screenshot of an external ultrasound image 300 of the same human thyroid shown in FIG. 3a, but with different image acquisition parameters 210. Specifically, line density has been increased, e.g., by using the "Res/Spd" control on a touch panel, where Res increases resolution (resulting in more transmit lines and a slower frame rate) and Spd increases speed (resulting in fewer transmit lines and a faster frame rate). Transmit frequency has also both been increased, e.g., by using the "2D Opt" (2D frequency option) control) on a touch panel, that changes the transmit/receive frequencies. As a result of these changes, the image exhibits improved spatial resolution and uniformity with reduced penetration, as can be seen for example in the crisper definition and higher resolution of the thyroid 310 and sternocleidomastoid 330, and their borders, as compared with FIG. 3a. The skin layer 350 and muscle layer 360 are also more clearly delineated.

Figure 4A:
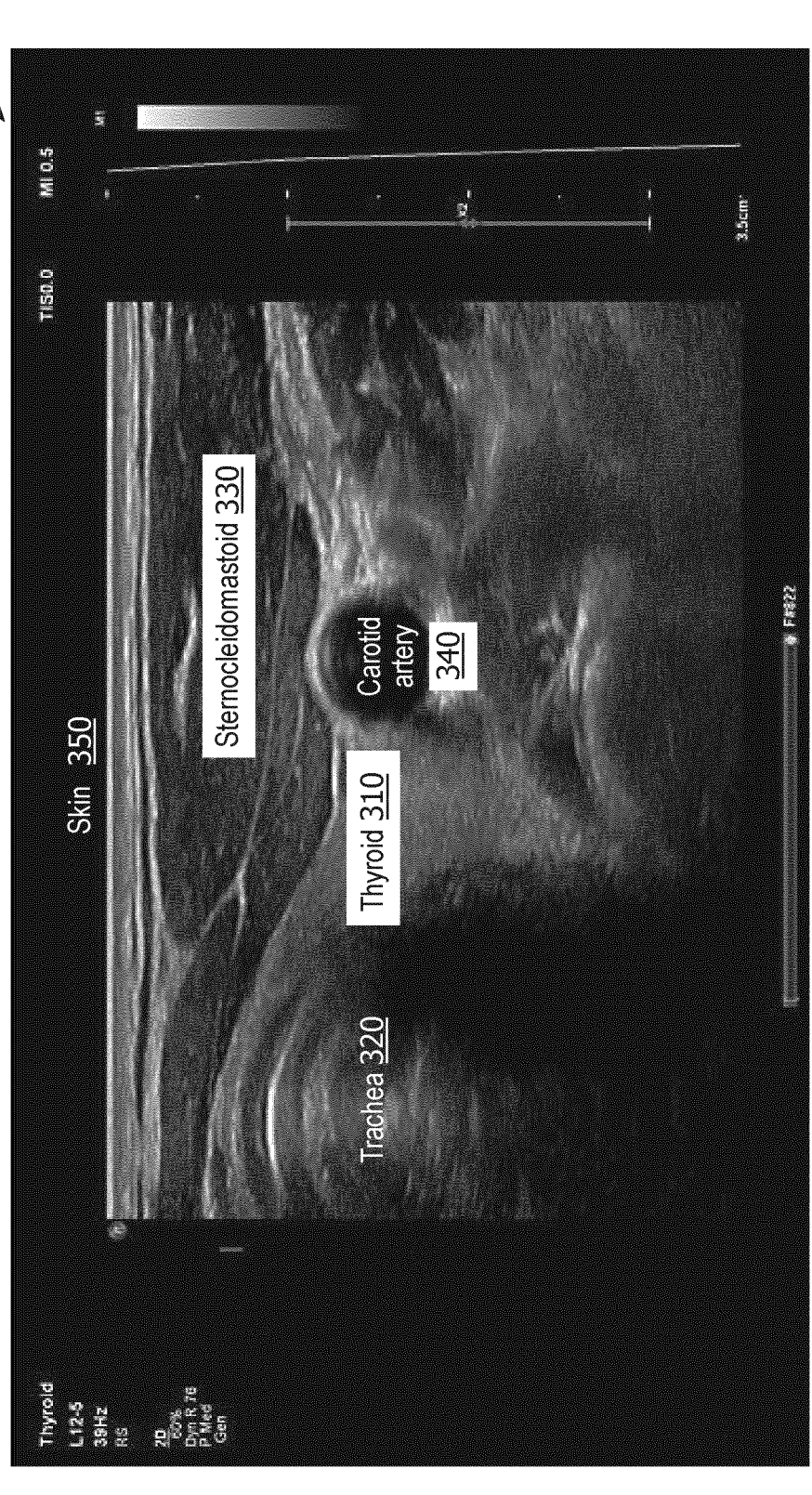
FIG. 4a is a screenshot of an external ultrasound image of a human thyroid, captured using default imaging parameters.

FIG. 4a is a screenshot of an external ultrasound image 300 of a human thyroid, captured using default imaging parameters. Visible are the thyroid 310, trachea 320, sternocleidomastoid 330, and carotid artery 340. The image shows room for improvement in tissue border definition and tissue contrast resolution of the thyroid 310.

Figure 4B:
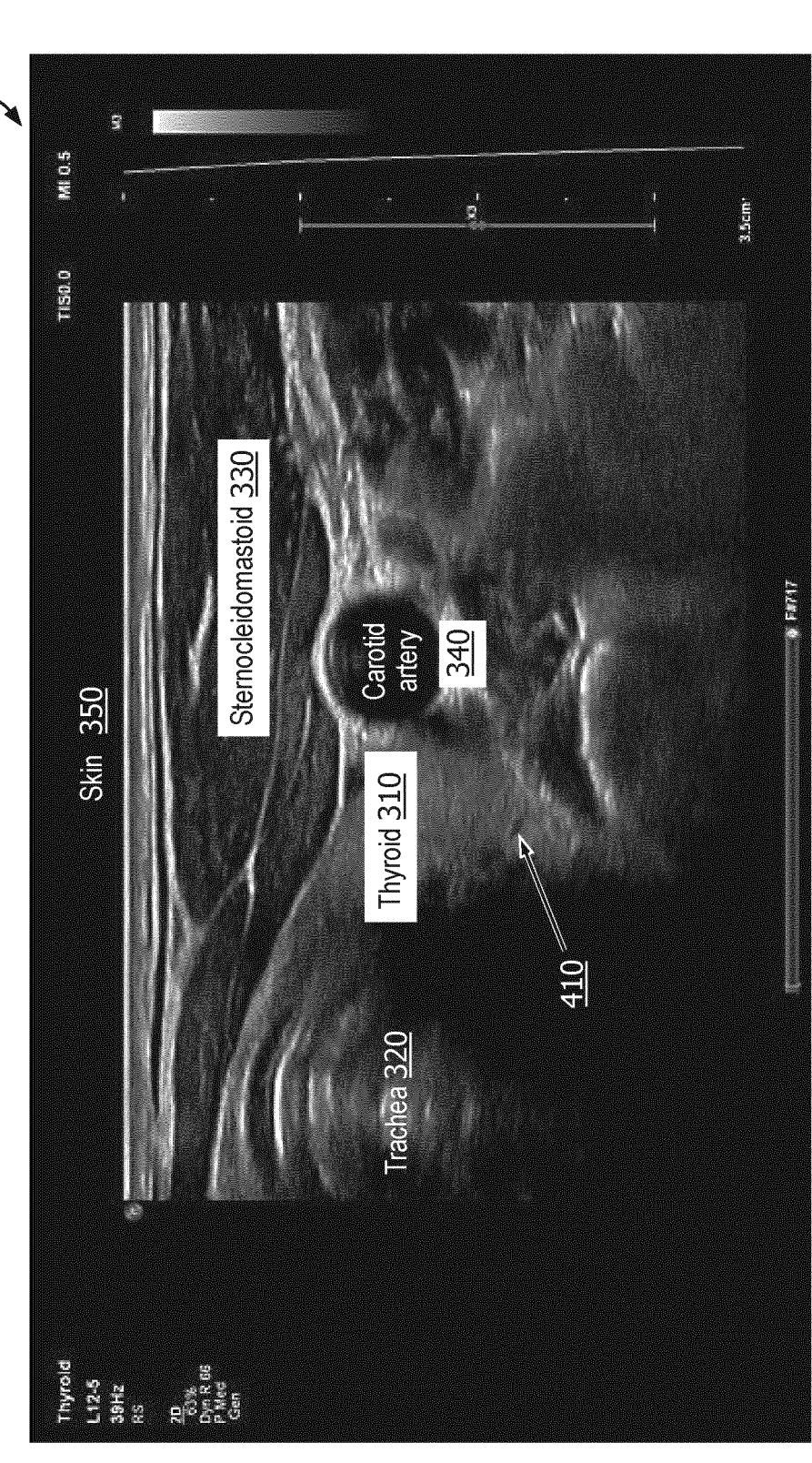
FIG. 4b is a screenshot of an external ultrasound image of the same human thyroid shown in FIG. 4a, but with different image post-processing parameters.

FIG. 4b is a screenshot of an external ultrasound image 300 of the same human thyroid shown in FIG. 4a, but with different image post-processing parameters 220. Specifically, the amount of image processing has been increased (e.g., via an XRES™ control on a touch panel), the dynamic range has been decreased (e.g., via a "Dyn Range" control on the touch panel), and the gray map has been shifted (e.g., via a "Gray Map" control on the touch panel), such that the image exhibits improved tissue border definition and tissue contrast resolution, as can be seen for example in the borders and internal texture of the thyroid 310 as compared to FIG. 4a. This improved visualization permits a mass 410 within the thyroid to be seen, that cannot be distinguished clearly in FIG. 4a.

Figure 5:
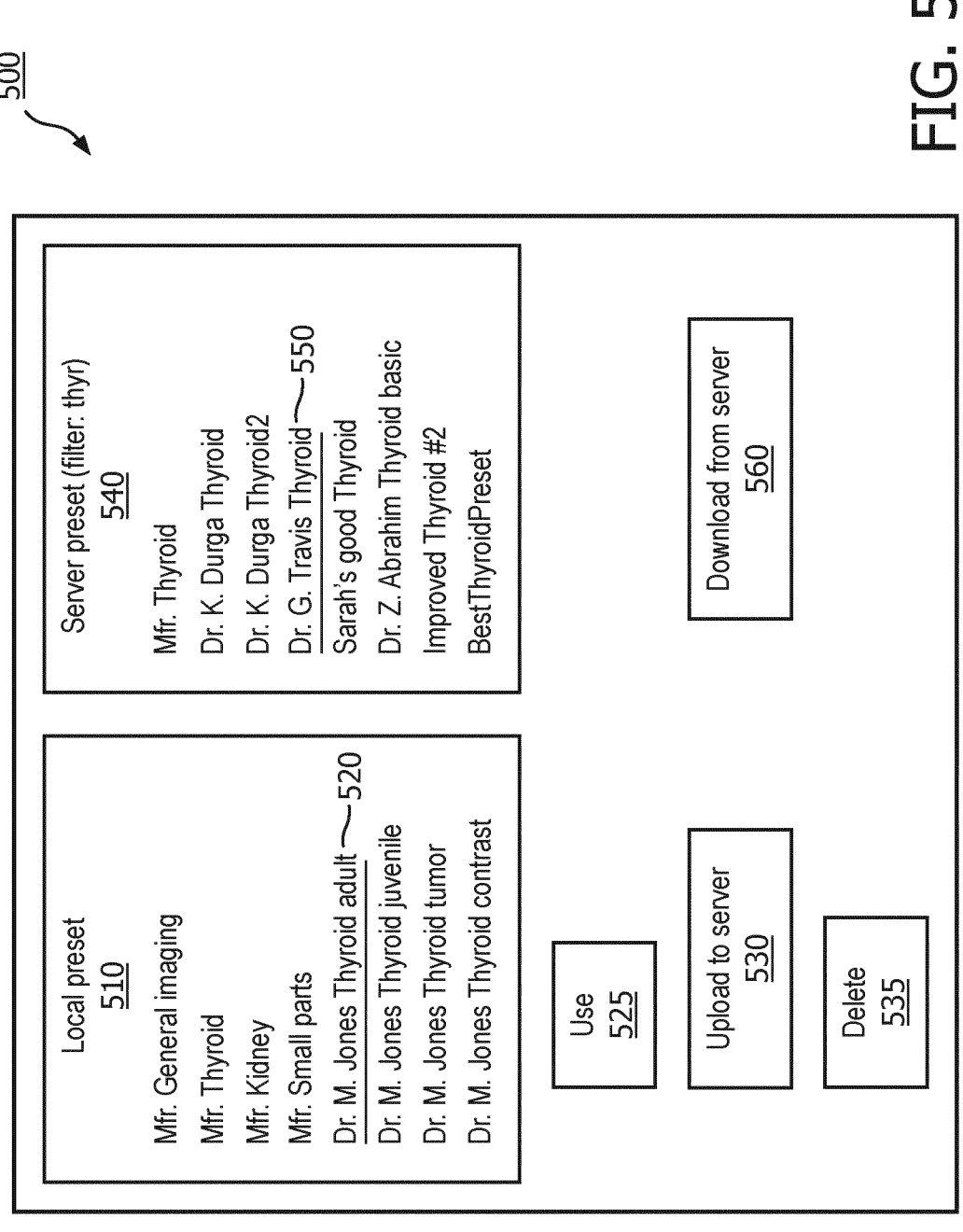
FIG. 5 is a display screen of an example ultrasound preset sharing system, according to at least one embodiment of the present disclosure.

FIG. 5 is a display screen 500 of an example ultrasound preset sharing system, according to at least one embodiment of the present disclosure. In this example, a user is able to select local presets 510 from a local storage medium (e.g., a non-volatile memory or hard disk drive. The parameters stored in the presently selected preset 520 may be loaded into the ultrasound imaging system 100 through activation of a Use button 525, or may be uploaded to the remote server via an Upload button 530, or deleted with e Delete button 535. The user is also able to select remote presets or server presets 540, which are stored on the remote server. Information on the server indicates to the local system that a given preset file is available for download. The presently selected preset 550 may, through activation of a Download button 560, be copied into the list of local presets 510, where it will be locally accessible. In some cases, downloaded preset files may be displayed as a different color, font, or style than manufacturer preset files and locally created preset files, to distinguish them as content generated by other users. Manufacturer preset files may be present on the system at the time of purchase, and may not be editable, although edited versions may be saves as new local presets and made available to other users over the network. In some embodiments, presets are only provided to remote users in the list of remote or server presets 540 after they have been reviewed/vetted by the manufacturer to ensure patient health and safety, as well as proper use of the ultrasound imaging equipment.

Other displays and user controls may be employed instead of or in addition to the example portrayed here. In some embodiments, each preset is saved along with an example image, thumbnail image, before and after images, or a difference or subtraction image comparing the before and after images, in addition to a title and description. In some embodiments, several different images may be uploaded to provide a sense of the capabilities, uses, and advantages of a particular custom preset file. In some embodiments, the ultrasound preset sharing system displays a comparison of the system's current settings and those of a selected preset. In some embodiments, the ultrasound preset sharing system displays a comparison of the settings in two different presets. In some embodiments, preset files can be selected from a menu containing only titles. In other embodiments, the selection menu may include descriptions, author names, author credentials, user ratings of the files, manufacturer ratings of the files, user comments on the files, manufacturer comments on the files, example images, number of times the preset has been downloaded, and other information as necessary to communicate the content, purpose, and utility of the preset files. In still other embodiments, descriptions, author names, author credentials, user ratings of the files, user comments on the files, manufacturer ratings of the files, manufacturer comments on the files, example images, and other information are available when a particular user control (e.g., a right mouse click) is activated on a particular preset filename.

In some embodiments, the remote server is configured to generate customized presets automatically, based on the pooled presets stored on the server. For example, the server may use artificial intelligence or other analysis methods to identify common elements or an average of settings for all presets containing the word "thyroid", and may then automatically generate a consensus or crowdsourced preset that includes these common features or averages. Alternatively, the manufacturer may observe, for example, that 80% of the presets uploaded by users for a particular application have a smoother image quality compared than that provided by the factory preset for the same application, can increase the smoothness setting in future releases of the factory preset for that application. The manufacturer may also start to understand the difference among different regions and can start to build geography-specific presets based on this information. The manufacturer can also perform analyses of the preset files, including but not limited to statistical analysis, data mining, and deep learning for all controls, to and find the preferred value for certain controls either overall or for particular regions, groups, or applications. The results of analysis can also help the manufacturer identify the most commonly customized controls. This information can help the manufacturer prioritize these controls. For example, if the XRES setting is the most commonly altered, the manufacturer provide more options under XRES, or can change the UI to make the XRES options more accessible. The analysis can be done in a region-specific manner (for example, Asian vs North America) or a facility-specific manner (for example, major hospitals vs small clinics) to understand differences among different regions or different facilities so that the manufacturer can start to build specific presets for these regions or groups.

In the example shown in FIG. 5, presets are identified by a file name or brief text description. However, in other embodiments presets may be uniquely identified by alphanumeric text, shape, symbol, etc., and/or combinations thereof. Other embodiments may include a preview pane similar to that shown in FIG. 2. In some embodiments, the server is configured to reject uploads that contain identical titles or image settings to files that currently exist on the server, or to issue a warning to users attempting to upload duplicate files. In some embodiments, only registered users are permitted access to the server, and registered users are permitted to enter comments or ratings of only those preset files they have downloaded. In some embodiments, the system is configured to enable the manufacturer to "push" custom presets to a group of ultrasound systems as a fashion similar to smart phone upgrade. In these embodiments, each individual user may have the option to install or reject the custom presets.

Figure 6:
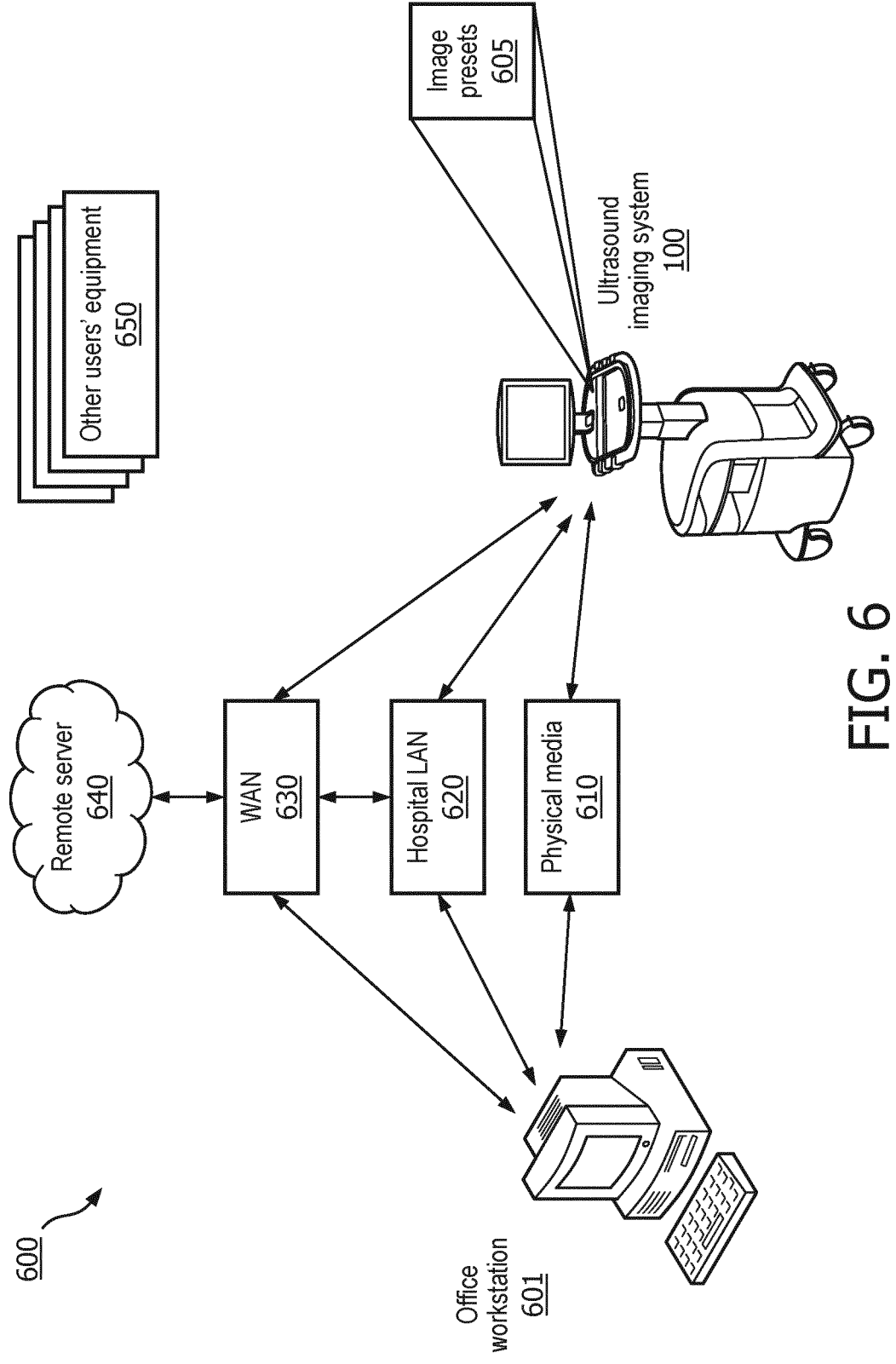
FIG. 6 is a schematic diagram of an ultrasound preset sharing system according to at least one embodiment of the present disclosure.

FIG. 6 is a schematic diagram of an ultrasound preset sharing system 600 according to at least one embodiment of the present disclosure. As described above, image presets 605 are stored and used within the ultrasound imaging system 100. These presets 605 may be stored (e.g., as backup copies) as files on physical data storage media 610 such as flash drives or optical discs. Image presets 605 may also be uploaded to, and stored on, a remote server 640, where the stored preset files 605 can serve as personal backups, and where they may also be accessible to the equipment of other users 650 (e.g., the laptop computers, workstations, mobile devices, and ultrasound imaging systems of other users). The other users 650 may download the presets 605 for use on their own ultrasound imaging systems. Presets 605 created by other users 650 and uploaded to the remote server 640 may also be downloaded from the remote server 640 to the ultrasound imaging system 100 for local use by clinicians and other users in medical imaging procedures and in postprocessing of medical images (e.g., for reporting or archival purposes).

In some implementations, the ultrasound imaging system 100 may communicate with the remote server directly via a wide-area network or WAN 630 (e.g., the Internet or a cellular data network). In other implementations, network access is restricted for the ultrasound imaging system 100 (e.g., to ensure the privacy of medical data and/or the physical and software integrity of the ultrasound imaging system 100). In these cases, communication with the remote server 640 may be through an office workstation 601. The office workstation 601 may be a laptop or desktop computer, a notebook or tablet computer, a smartphone, a handheld device, or other computing device capable of accessing a wide-area network 630. Image preset files 605 may be transferred to the office workstation 601 via physical media 610, or via a local-area network or LAN 620. Examples of the LAN 620 may include but are not limited to a Digital Imaging and Communications in Medicine (DICOM) system, a Picture Archiving and Communication System (PACS), and/or a Hospital Information System (HIS), accessed via a network connection. In some instances it may also be possible for the ultrasound system 100 to communicate with the office workstation 601 through a wide-area network 630.

In an example, a clinician or other user creates an image preset file 605 for a particular clinical application (e.g., imaging through a patient's skin to observe bone screws located within the patient's body). The preset file 605 may contain one or more image acquisition presets or one or more image post-processing presets, or any combination thereof, tailored to maximize the quality of ultrasound images acquired and stored for that application. The user then saves the image preset file 605 to a flash drive 610, and from the flash drive 610 to the office workstation 201. From the office workstation 601, the user uploads the image preset file 605 to the remote server 640 via the Internet 630, along with a title and description. The image preset file 605 is now accessible to the user via the remote server 640 as a backup or archive file. The image preset file 605 is also accessible to other users 650, who may read the title and description and download the preset file 605 for use on their own ultrasound imaging systems 100. Other users may give a rating to the preset file (e.g., on a scale of 0-5 stars), and the remote server 640 is capable of displaying the average rating, the number of ratings, rating statistics (e.g., a histogram), and a list of individual ratings. In some implementations, users may also leave a short text review of the preset file 605, to help guide or advise other users in the use or non-use of the image preset file 605.

In another example, a remote user 650 uploads an image preset file 605 to the remote server, and a local user operating an office workstation 601 reads the description of the image preset file 605 and decides to download it. The server 640 then copies the preset file 605 to the office workstation 601, which stores it in the list of local presets 510.

Figure 7:
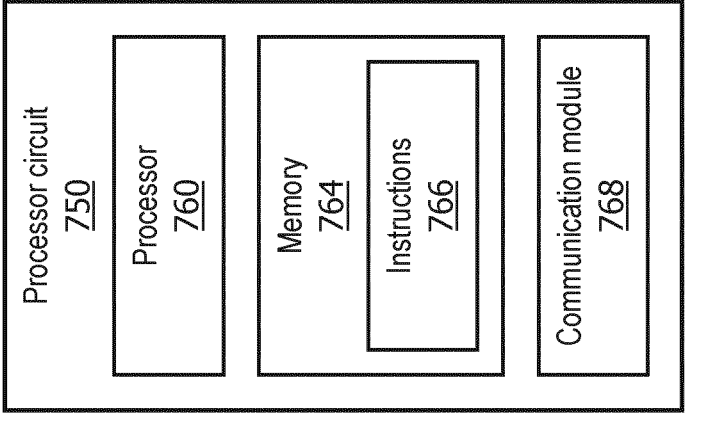
FIG. 7 is a schematic diagram of a processor circuit, according to embodiments of the present disclosure.

FIG. 7 is a schematic diagram of a processor circuit 750, according to embodiments of the present disclosure. The processor circuit 750 may be implemented in any of the ultrasound imaging system 100, office workstation 601, remote server 640, or other user's equipment 650, or other devices or workstations (e.g., third-party workstations, network routers, etc.) as necessary to implement the method. As shown, the processor circuit 750 may include a processor 760, a memory 764, and a communication module 768. These elements may be in direct or indirect communication with each other, for example via one or more buses.

The processor 760 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 760 may also comprise another hardware device, a firmware device, or any combination thereof configured to perform the operations described herein. The processor 760 may also be implemented as a combination of computing devices, e.g., a combination of a DSP and a microprocessor, a plurality of microprocessors, one or more microprocessors in conjunction with a DSP core, or any other such configuration.

The memory 764 may include a cache memory (e.g., a cache memory of the processor 760), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 764 includes a non-transitory computer-readable medium. The memory 764 may store instructions 766. The instructions 766 may include instructions that, when executed by the processor 760, cause the processor 760 to perform the operations described herein with reference the ultrasound imaging system 100, office workstation 601, remote server 640, or other user's equipment 650. Instructions 766 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 768 can include any electronic circuitry and/or logic circuitry to facilitate direct or indirect communication of data between the processor circuit 750, the ultrasound probe 108, the display 106, the networks 620 and 630, the physical media 610, and other processors located in other components of the ultrasound preset sharing system. In that regard, the communication module 768 can be an input/output (I/O) device. In some instances, the communication module 768 facilitates direct or indirect communication between various elements of the processor circuit 750 and/or the ultrasound imaging system 100, office workstation 601, remote server 640, LAN 620, WAN 630, and other users' equipment 650. The communication module 768 may communicate within the processor circuit 750 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media 610 such as a USB flash drive or memory stick.

An image preset can be used to automatically select values for individual imaging parameters, thus affecting how images are captured and displayed. Thus a user can advantageously avoid having to individually set each value. In some embodiments, when the user wants to individually adjust the values, even when using the preset, the user can do so with the UI shown in FIGS. 8-11.

Figure 8:
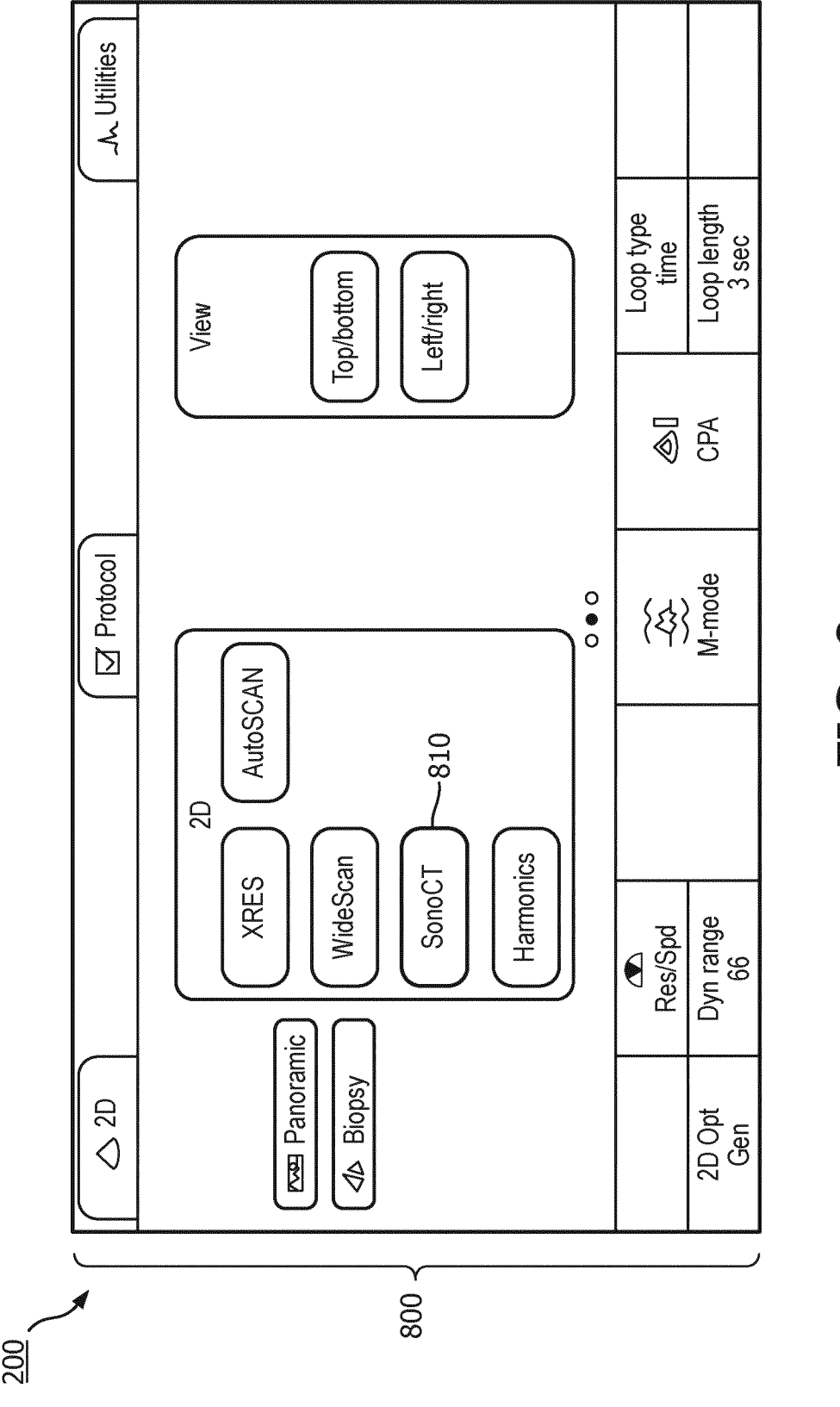
FIG. 8 is a display screen of an example ultrasound preset sharing system, according to at least one embodiment of the present disclosure.

FIG. 8 is a display screen 200 of an example ultrasound preset sharing system, according to at least one embodiment of the present disclosure. The display screen 200 allows users to adjust image parameters 800 that include image acquisition parameters 210 and image post-processing parameters 220 that, for aesthetic and functional reasons, have been comingled together rather than grouped separately. In this example, the SonoCT option 810 has been selected. SonoCT can refer to coplanar tomographic imaging, which uses beam steering to capture images at multiple angles without moving the ultrasound probe.

Figure 9:
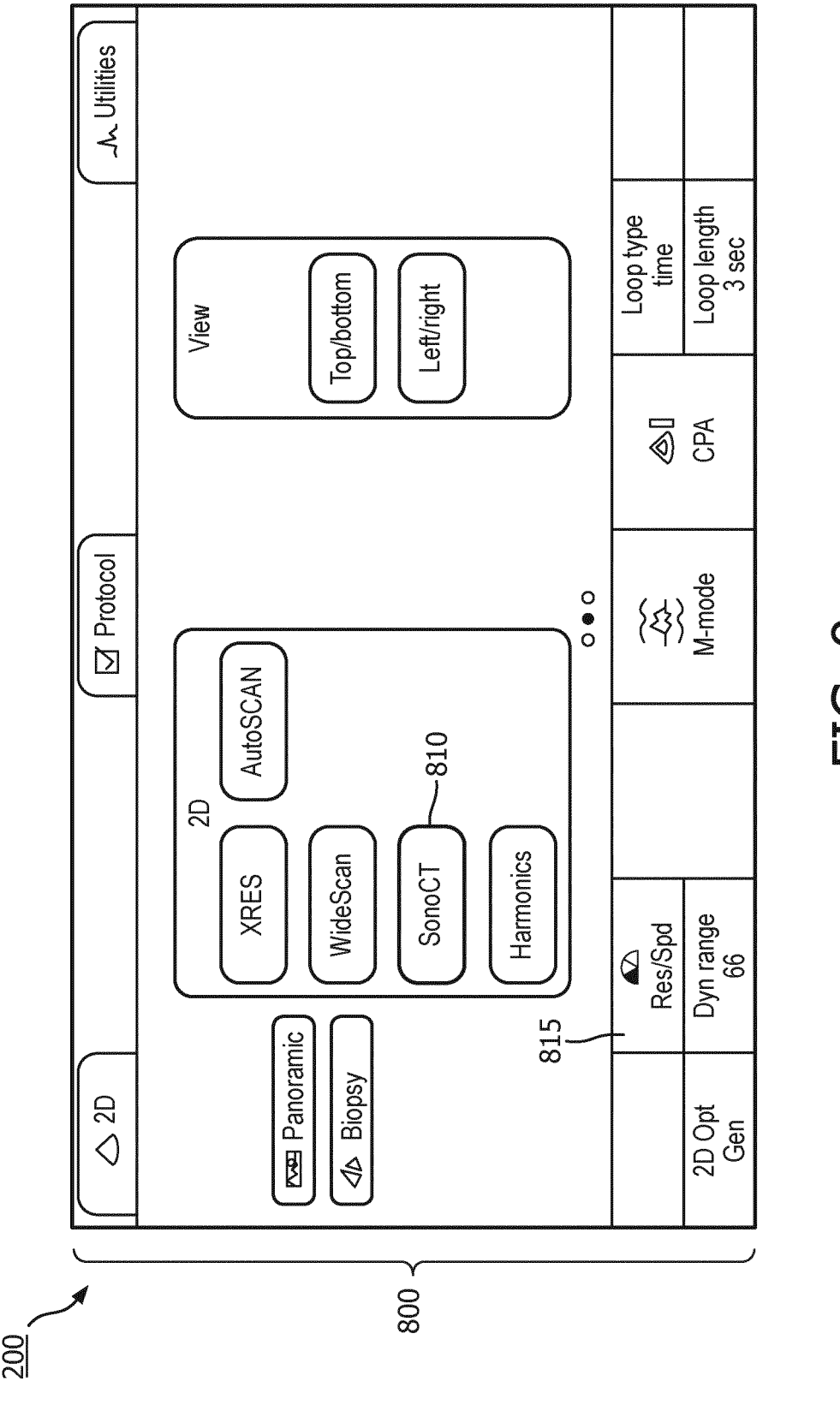
FIG. 9 is a display screen of an example ultrasound preset sharing system, according to at least one embodiment of the present disclosure.

FIG. 9 is a display screen 200 of an example ultrasound preset sharing system, according to at least one embodiment of the present disclosure. In this example, the SonoCT option 810 has been selected, and the Res/Spd setting 815 has been set to a lower value than in FIG. 8.

Figure 10:
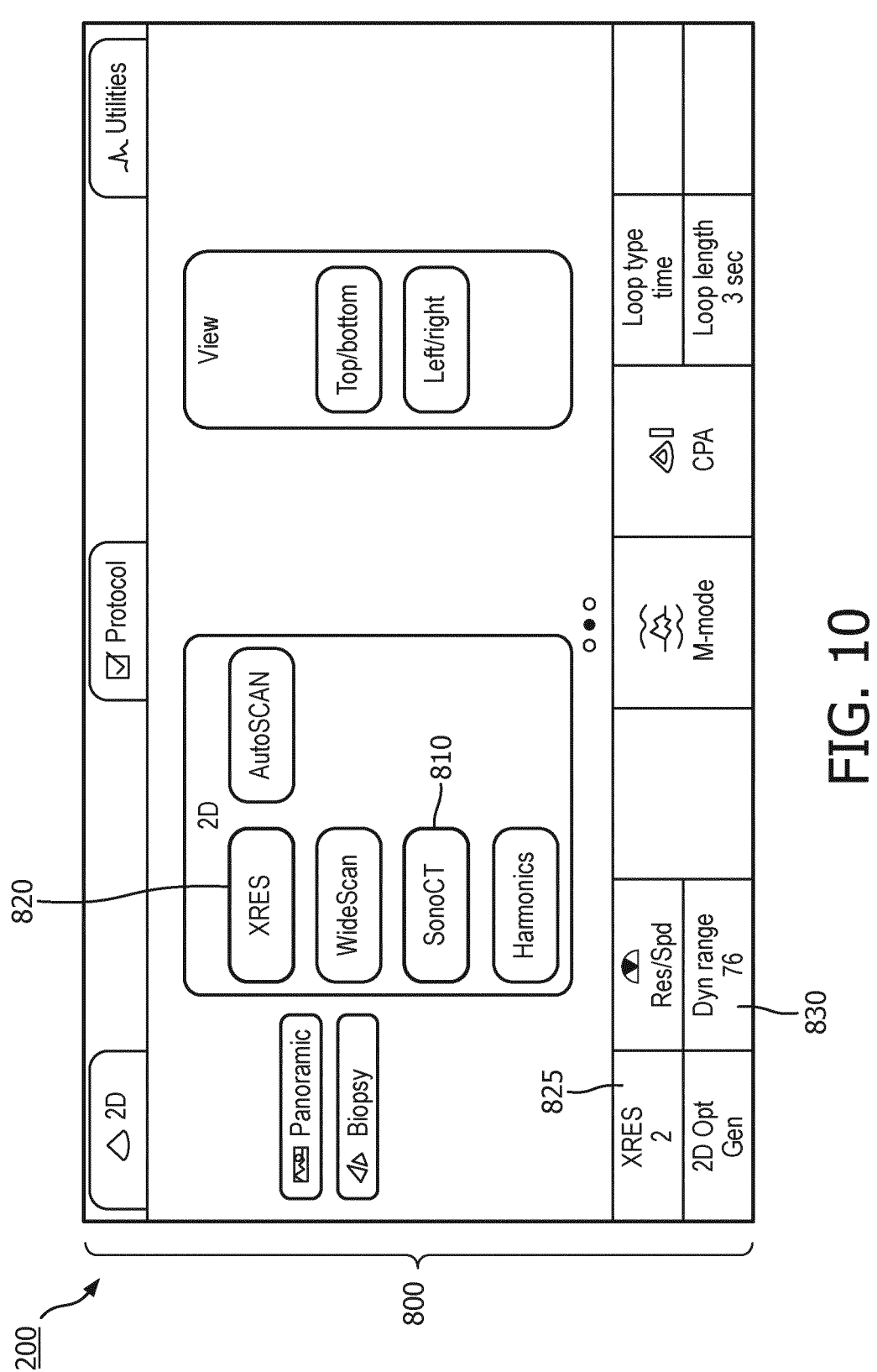
FIG. 10 is a display screen of an example ultrasound preset sharing system, according to at least one embodiment of the present disclosure.

FIG. 10 is a display screen 200 of an example ultrasound preset sharing system, according to at least one embodiment of the present disclosure. In this example, the SonoCT option 810 and XRES option 820 have been selected, an XRES value 825 has been set to 2, and a Dynamic Range value 830 has been set to 76.

Figure 11:
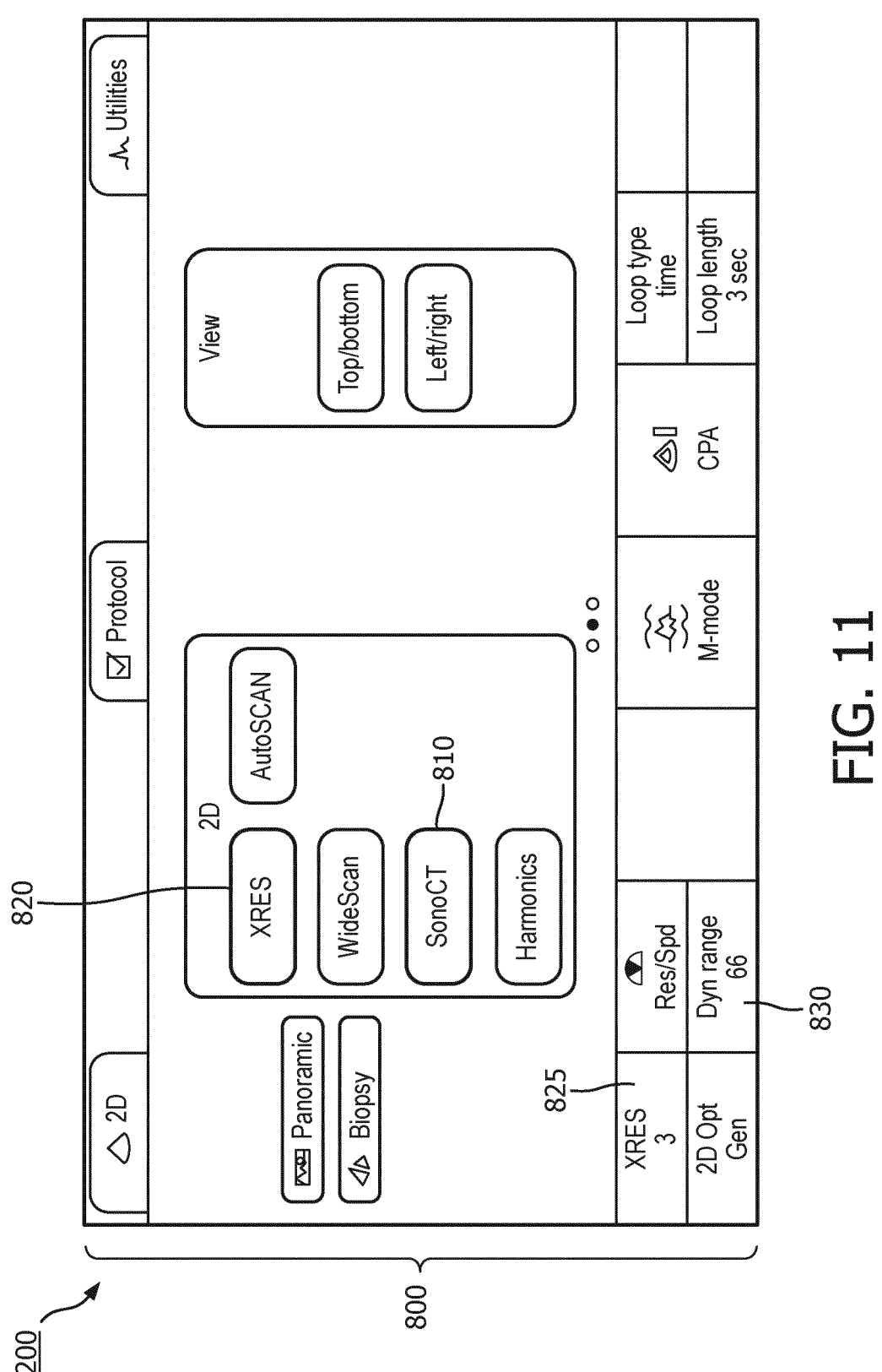
FIG. 11 is a display screen of an example ultrasound preset sharing system, according to at least one embodiment of the present disclosure.

FIG. 11 is a display screen 200 of an example ultrasound preset sharing system, according to at least one embodiment of the present disclosure. In this example, the SonoCT option 810 and XRES option 820 have been selected, the XRES value 825 has been increased to 3, and the Dynamic Range value 830 has been decreased to 66.

Figure 12:
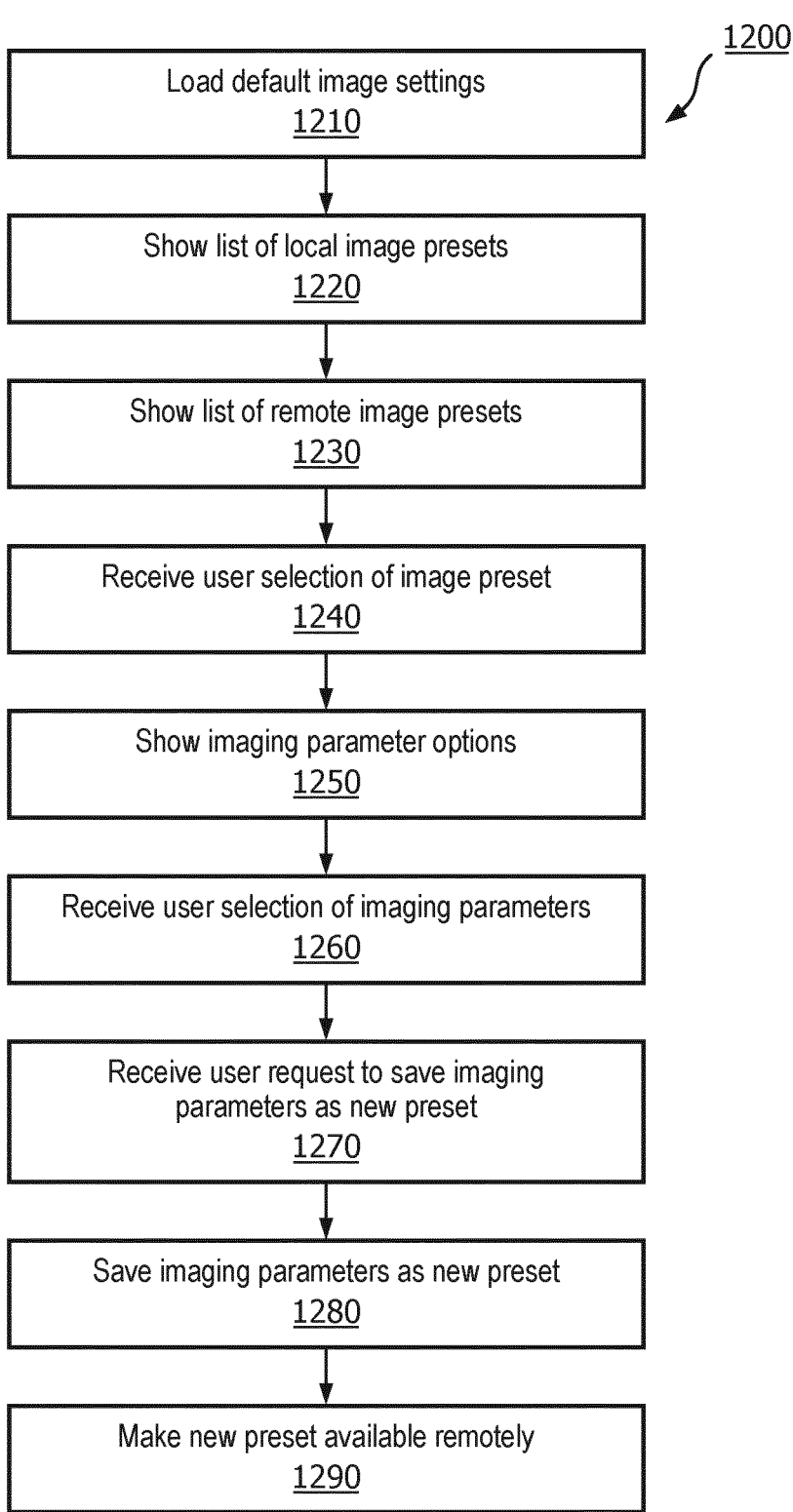
FIG. 12 is a flow diagram of an example ultrasound preset sharing method, according to at least one embodiment of the present disclosure.

FIG. 12 is a flow diagram of an example ultrasound preset sharing method 1200, according to at least one embodiment of the present disclosure. As illustrated, the method 1200 includes a number of enumerated steps, but embodiments of the method 1200 may include additional steps before, after, and in between the enumerated steps. In some embodiments, one or more of the enumerated steps may be omitted, performed in a different order, or performed concurrently. The steps of the method 1200 can be performed by processor circuit (e.g., processor circuit 750 of FIG. 7) implemented on an ultrasound console (e.g., ultrasound imaging system 100), a computer (e.g., office workstation 601), and/or a remote server in communication with multiple ultrasound consoles and/or workstations (e.g., remove server 640).

In step 1210, the method loads default image settings to be employed by the system. In step 1220, the method displays for the user a list of image presets that are available on the local system, as shown for example in FIG. 5. In step 1230, the method displays for the user a list of image presets that are available remotely, as shown for example in FIG. 5. Data or information available from the remote server over the network causes an ultrasound imaging console to recognize that the imaging preset is stored in the server memory and is available for download. A list of available imaging presets can thus be compiled and displayed. In step 1240, the method receives a user input selecting one of the local or remote image presets to be applied to the current image, or the current imaging procedure. This could for example be touch inputs on a touch screen or trackpad/mouse/button/knob inputs. In step 1250, the method displays to the user a menu or other selection of available imaging parameter options, as shown for example in FIG. 2. In step 1260, the method receives a user selection of imaging parameters (e.g., through user manipulation of sliders, buttons, softkeys, menus, etc.) This could be touch inputs on a touch screen or trackpad/mouse/button/knob inputs that are changing values of the parameter shown on the GUI as shown for example in FIG. 2. In some embodiments, the imaging console can preview what the effect of applying different parameters or presets to the current ultrasound image or imaging procedure. This could be on the same UI screen or separate UI screens. In step 1270, the method receives a user request to save the imaging parameters as a new preset (as shown for example in FIG. 2). In step 1280, the method saves the imaging parameters as a new preset that will be available to the local system. In step 1290, the method makes the new preset available to remote users over the network, as shown for example in FIG. 6.

As will be readily appreciated by those having ordinary skill in the art after becoming familiar with the teachings herein, the ultrasound preset sharing system addresses numerous concerns in the art, by providing users with a system to share their imaging expertise with one another, and to rapidly receive imaging expertise from other users, while simultaneously providing manufacturers of ultrasound imaging systems with a system for distributing image presets and other information co-developed with the aid of skilled users. A number of variations are possible on the examples and embodiments described above. For example, the remote server can be used for sharing other information as well, including but not limited to protocols, user-defined calculation packages, and other customized settings such as UI layout (moving buttons) and workflow. Further, the system may be employed to share imaging presets for other types of medical imaging systems, including but not limited to intravascular ultrasound (IVUS), intracardiac echocardiography (ICE), transesophageal echocardiography (TEE), x-ray, computed tomography (CT), and magnetic resonance imaging (MRI). In some embodiments, the medical imaging system can obtain images of the patient body while positioned outside of the patient body. In some embodiments, the medical imaging system can obtain images of the patient body while positioned inside the patient body using, e.g., catheter, guide wire, guide catheter, and/or other intraluminal imaging device.

Accordingly, the logical operations making up the embodiments of the technology described herein are referred to variously as operations, steps, objects, elements, components, or modules. Furthermore, it should be understood that these may be performed in any order, unless explicitly claimed otherwise or a specific order is inherently necessitated by the claim language.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the ultrasound preset sharing system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the ultrasound preset sharing system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting.

Changes in detail or structure may be made without departing from the basic elements of the subject matter as defined in the following claims.

What is claimed is:

1. An ultrasound imaging system, comprising:

an external server configured to provide user-to-user sharing of a user-created custom ultrasound setting between remote ultrasound imaging consoles, wherein the remote ultrasound imaging consoles comprise a first ultrasound imaging console at a first location and a different, second ultrasound imaging console at a second location remote from the first location, wherein the external server is at a third location remote from the first location and the second location, wherein the external server comprises a processor in communication with a memory, wherein the processor is configured to:

receive, from the first ultrasound imaging console, an upload request for the user-created custom ultrasound setting, wherein the user-created custom ultrasound setting is created by a first user at the first ultrasound imaging console;

receive, from the first ultrasound imaging console, the user-created custom ultrasound setting;

store the user-created custom ultrasound setting in the memory, wherein the memory is configured to store a plurality of user-created custom ultrasound settings created by a plurality of users;

output, to the second ultrasound imaging console, data representative of the user-created custom ultrasound setting such that the user-created custom ultrasound setting created by the first user is available to a different, second user at the second ultrasound imaging console;

receive, from the second ultrasound imaging console, a request for the user-created custom ultrasound setting;

retrieve, from the memory, the user-created custom ultrasound setting in response to the request; and output, to the second ultrasound imaging console, the user-created custom ultrasound setting.

2. The ultrasound imaging system of claim 1, wherein the user-created custom ultrasound setting is different than a manufacturer ultrasound setting.

3. The ultrasound imaging system of claim 1, wherein the processor is further configured to:

receive, from a plurality of ultrasound imaging consoles, a plurality of requests to upload the plurality of user-created custom ultrasound settings;

receive, from the plurality of ultrasound imaging consoles, the plurality of user-created custom ultrasound settings;

store the plurality of user-created custom ultrasound settings in the memory;

output, to the plurality of ultrasound imaging consoles, data representative of each of the plurality of user-created custom ultrasound settings;

receive, from one or more of the plurality of ultrasound imaging consoles, a selection of one or more of the plurality of user-created custom ultrasound settings to download; and output, to the one or more of the plurality of ultrasound imaging consoles, the one or more of the plurality of user-created custom ultrasound settings.

4. The ultrasound imaging system of claim 1, wherein the processor is further configured to:

receive, from a manufacturer system, a manufacturer ultrasound setting, wherein the manufacturer ultrasound setting is different from the user-created custom ultrasound setting;

store the manufacturer ultrasound setting in the memory;

output, to a plurality of ultrasound imaging consoles, data representative of the manufacturer ultrasound setting;

receive, from one or more of the plurality of ultrasound imaging consoles, a selection of the manufacturer ultrasound setting to download; and output, to the one or more of the plurality of ultrasound imaging consoles, the manufacturer ultrasound setting.

5. The ultrasound imaging system of claim 1, further comprising the first ultrasound imaging console and the second ultrasound imaging console, wherein the first ultrasound imaging console comprises:

a display;

a processor configured to:

generate a first ultrasound image based on the user-created custom ultrasound setting using first ultrasound image data acquired by a first ultrasound imaging probe, wherein the user-created custom ultrasound setting comprises a post-processing parameter defining how the first ultrasound image is displayed and not defining operation of the first ultrasound imaging probe to acquire the first ultrasound image data; and output, to the display, a graphical user interface (GUI) comprising an indication of the user-created custom ultrasound setting and an upload option; and a communication module configured to output an upload request for the user-created custom ultrasound setting based on user selections of the indication of the user-created custom ultrasound setting and the upload option;

wherein the second ultrasound imaging console is configured to:

generate a second ultrasound image based on the user-created custom ultrasound setting using different, second ultrasound image data acquired by a different, second ultrasound imaging probe; and show the second ultrasound image on a display according to the post-processing parameter.

6. The ultrasound imaging system of claim 5, wherein the processor of the first ultrasound imaging console is configured to receive a user input, via the GUI, to modify the user-created custom ultrasound setting.

7. The ultrasound imaging system of claim 6, wherein the first ultrasound imaging console comprises a memory, wherein the processor of the first ultrasound imaging console is configured to:

store the user-created custom ultrasound setting in the memory of the first ultrasound imaging console;

retrieve the user-created custom ultrasound setting from the memory of the first ultrasound imaging console based on the upload request; and output the user-created custom ultrasound setting to the external server.

8. The ultrasound imaging system of claim 5, wherein the second ultrasound imaging console comprises:

a display; and a processor configured to:

output, to the display of the second ultrasound imaging console, a graphical user interface (GUI) comprising a download option and an indication of the user-created custom ultrasound setting based on the data representative of the user-created custom ultrasound setting; and output a download request to the external server based on a user selection of the download option and the indication of the user-created custom ultrasound setting.

9. The ultrasound imaging system of claim 8, wherein the second ultrasound imaging console comprises a memory, wherein the processor of the second ultrasound imaging console is configured to:

store the user-created custom ultrasound setting in the memory of the second ultrasound imaging console;

retrieve the user-created custom ultrasound setting from the memory of the second ultrasound imaging console based on an implementation request; and apply the user-created custom ultrasound setting to generate the second ultrasound image with the user-created custom ultrasound setting.

10. The ultrasound imaging system of claim 5, further comprising:

the first ultrasound imaging probe, wherein the first ultrasound imaging probe is in communication with the first ultrasound imaging console; and the second ultrasound imaging probe, wherein the second ultrasound imaging probe is in communication with the second ultrasound imaging console.

11. The ultrasound imaging system of claim 5, wherein the user-created custom ultrasound setting comprises an acquisition parameter defining the operation of the first ultrasound imaging probe to acquire the first ultrasound image data.

12. An ultrasound imaging method, comprising:

receiving, at an external server comprising a processor in communication with a memory, an upload request for a user-created custom ultrasound setting, wherein the external server provides user-to-user sharing of the user-created custom ultrasound setting between remote ultrasound imaging consoles, wherein the remote ultrasound imaging consoles comprise a first ultrasound imaging console at a first location and a different, second ultrasound imaging console at a second location remote from the first location, wherein the external server is at a third location remote from the first location and the second location, wherein the upload request is received from the first ultrasound imaging console, wherein the user-created custom ultrasound setting is created by a first user at the first ultrasound imaging console;

receiving, at the external server, the user-created custom ultrasound setting from the first ultrasound imaging console;

storing the user-created custom ultrasound setting in the memory, wherein the memory stores a plurality of user-created custom ultrasound settings created by a plurality of users;

outputting, by the external server, data representative of the user-created custom ultrasound setting to the second ultrasound imaging console such that the user-created custom ultrasound setting created by the first user is available to a different, second user at the second ultrasound imaging console;

receiving, at the external server, a request for the user-created custom ultrasound setting from the second ultrasound imaging console;

retrieving, from the memory, the user-created custom ultrasound setting in response to the request; and outputting, by the external server, the user-created custom ultrasound setting to the second ultrasound imaging console.

13. The ultrasound imaging method of claim 12, further comprising:

receiving, at the external server, a plurality of requests to upload the plurality of user-created custom ultrasound settings from a plurality of ultrasound imaging consoles;

receiving, at the external server, the plurality of user-created custom ultrasound settings from the plurality of ultrasound imaging consoles;

storing the plurality of user-created custom ultrasound settings in the memory;

outputting, by the external server, data representative of each of the plurality of user-created custom ultrasound settings to the plurality of ultrasound imaging consoles;

receiving, at the external server, a selection of one or more of the plurality of user-created custom ultrasound settings to download from one or more of the plurality of ultrasound imaging consoles; and outputting, by the external server, the one or more of the plurality of user-created custom ultrasound settings to the one or more of the plurality of ultrasound imaging consoles.

14. The ultrasound imaging method of claim 12, further comprising:

receiving, at the external server, a manufacturer ultrasound setting from a manufacturer system, wherein the manufacturer ultrasound setting is different from the user-created custom ultrasound setting;

storing the manufacturer ultrasound setting in the memory;

outputting, from the external server, to a plurality of ultrasound imaging consoles, data representative of the manufacturer ultrasound setting;

receiving, at the external server, a selection of the manufacturer ultrasound setting to download from one or more of the plurality of ultrasound imaging consoles; and outputting, by the external server, the manufacturer ultrasound setting to the one or more of the plurality of ultrasound imaging consoles.

15. The ultrasound imaging method of claim 12, further comprising:

generating, by a processor of the first ultrasound imaging console, a first ultrasound image based on the user-created custom ultrasound setting using first ultrasound image data acquired by a first ultrasound imaging probe, wherein the user-created custom ultrasound setting comprises a post-processing parameter defining how the first ultrasound image is displayed and not defining operation of the first ultrasound imaging probe to acquire the first ultrasound image data;

outputting, by the processor of the first ultrasound imaging console, a graphical user interface (GUI) to a display of the first ultrasound imaging console, wherein the GUI comprises an indication of the user-created custom ultrasound setting and an upload option;

outputting, by the processor of the first ultrasound imaging console, the upload request to the external server based on user selections of the indication of the user-created custom ultrasound setting and the upload option;

generating, by the second ultrasound imaging console, a second ultrasound image based on the user-created custom ultrasound setting using different, second ultrasound image data acquired by a different, second ultrasound imaging probe; and showing, by the second ultrasound imaging console, the second ultrasound image on a display according to the post-processing parameter.

16. The ultrasound imaging method of claim 15, wherein the user-created custom ultrasound setting comprises an acquisition parameter defining the operation of the first ultrasound imaging probe to acquire the first ultrasound image data.

17. The ultrasound imaging method of claim 15, further comprising:

receiving, at the processor of the first ultrasound imaging console, a user input to modify the user-created custom ultrasound setting via the GUI.

18. The ultrasound imaging method of claim 17, further comprising:

storing, by the processor of the first ultrasound imaging console, the user-created custom ultrasound setting in a memory of the first ultrasound imaging console;

retrieving, by the processor of the first ultrasound imaging console, the user-created custom ultrasound setting from the memory of the first ultrasound imaging console based on the upload request; and outputting, by the processor of the first ultrasound imaging console, the user-created custom ultrasound setting to the external server.

19. The ultrasound imaging system of claim 1, wherein the first location comprises a first facility and the second location comprises a second facility remote from the first facility.

* * * * *